United States Patent [19]

Shishido et al.

[11] 4,113,495

[45] Sep. 12, 1978

[54] COLOR PHOTOGRAPHIC LIGHT-SENSITIVE MATERIAL CAPABLE OF PROVIDING STABLE COLOR IMAGES

[75] Inventors: Tadao Shishido; Hiroshi Hara; Atsuaki Arai, all of Minami-ashigara, Japan

[73] Assignee: Fuji Photo Film Co., Ltd., Minami-ashigara, Japan

[21] Appl. No.: 806,121

[22] Filed: Jun. 13, 1977

[30] Foreign Application Priority Data

Jun. 11, 1976 [JP] Japan .................. 51-69148

[51] Int. Cl.² .................. G03C 1/40; G03C 7/00
[52] U.S. Cl. .................. 96/100 R; 96/56; 96/56.5; 96/74
[58] Field of Search .................. 96/56, 56.5, 74, 100

[56] References Cited

U.S. PATENT DOCUMENTS

| | | | |
|---|---|---|---|
| 3,432,300 | 3/1969 | Lestina et al. | 96/56 |
| 3,698,909 | 10/1972 | Lestina et al. | 96/100 |
| 3,930,866 | 1/1976 | Oishi et al. | 96/56.5 |
| 3,935,015 | 1/1976 | Arai et al. | 96/56 |
| 4,015,990 | 4/1977 | Ishida et al. | 96/56 |

Primary Examiner—Travis Brown
Attorney, Agent, or Firm—Sughrue, Rothwell, Mion, Zinn and MacPeak

[57] ABSTRACT

A color photographic light-sensitive material containing a coupler therein and, in at least one photographic layer, a compound represented by the following general formula (I):

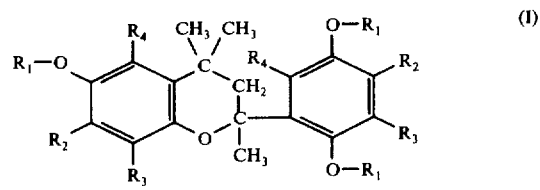

wherein $R_1$ represents a hydrogen atom or an —X—Y group wherein X represents a carbonyl group or a sulfonyl group, and Y represents a straight chain, branched chain or cyclic alkyl group having 1 to 20 carbon atoms, an aryl group, an aralkyl group, an alkoxy group containing a straight chain, branched chain or cyclic alkyl group having 1 to 20 carbon atoms, an aryloxy group, an aralkoxy group, a straight chain, branched chain or cyclic alkoxycarbonyl group having 2 to 20 carbon atoms, an aryloxycarbonyl group or an aralkoxycarbonyl group; and $R_2$, $R_3$ and $R_4$, which may be the same or different, each represents a hydrogen atom, a straight chain, branched chain or cyclic alkyl group having 1 to 20 carbon atoms, a straight chain, branched chain or cyclic alkoxy group having 1 to 20 carbon atoms, an aryl group, an aryloxy group, an aralkyl group, an aralkoxy group, an alkenyl group, an alkenoxy group, an acylamino group, a halogen atom, an alkylthio group containing a straight chain, branched chain or cyclic alkyl group having 1 to 20 carbon atoms, an aryl group, a diacylamino group, an acyl group having 1 to 20 carbon atoms, a sulfonamido group, a straight chain, a branched chain or cyclic alkylamino group containing a straight chain or branched chain alkyl group having 1 to 20 carbon atoms, a straight chain, branched chain or cyclic alkoxycarbonyl group having 2 to 20 carbon atoms or an acyloxy group having 1 to 20 carbon atoms, provided that $R_2$, $R_3$ and $R_4$ do not simultaneously represent hydrogen atoms.

16 Claims, No Drawings

COLOR PHOTOGRAPHIC LIGHT-SENSITIVE MATERIAL CAPABLE OF PROVIDING STABLE COLOR IMAGES

BACKGROUND OF THE INVENTION

1. FIELD OF THE INVENTION

The present invention relates to a color photographic light-sensitive material and, more particularly, it relates to preventing fading of dye images finally obtained by development-processing a color photographic light-sensitive material and preventing discoloration of uncolored areas (hereinafter referred to as white background).

2. DESCRIPTION OF THE PRIOR ART

Color images obtained by photographically processing a silver halide color photographic light-sensitive material comprise, in general, an azomethine dye or indoaniline dye image formed by the reaction between an oxidation product of an aromatic primary amine developing agent and a coupler.

The thus-obtained color photographic images are stored for a long time as records or to be displayed. However, these photographic images are not necessarily stable to light, humidity or heat and, when exposed to light for a long time or stored under high temperature and high humidity conditions, the dye images tend to fade or discolor and, in addition, the white background is changed to yellow, usually resulting in a deterioration of image quality.

This fading and discoloration of images are quite serious defects in a recording material. The following compounds have heretofore been used to remove these defects. For example, hydroquinone derivatives including 2,5-di-tertbutylhydroquinone, phenol derivatives such as 2,6-di-tertbutyl-p-cresol, 4,4'-methylenebis(2,6-di-tert-butylphenol), 2,2'-methylenebis(4-ethyl-6-tert-butylphenol), 4,4'-isopropylidenediphenol, etc., and tocopherols are representative of such compounds.

These compounds are effective to some extent as an agent which prevents fading or discoloration of dye images. However, the effect is not completely satisfactory or, although some compounds may prevent fading, they deteriorate hue, generate fog, lower dispersion property or form crystals. Thus, no satisfactory color image stabilizers which exhibit completely excellent effects for photographic use are known.

SUMMARY OF THE INVENTION

An object of the present invention is to provide a color photographic light-sensitive material capable of providing stable color images which comprises a color photographic light-sensitive material containing a color coupler therein and in at least one photographic layer a color image stabilizer having an effect sufficient for preventing fading or discoloration of color images.

As a result of various investigations, it has now been discovered that the objects of the present invention are attained by the incorporation in at least one photographic layer of a color photographic light-sensitive material containing a color coupler therein of a compound represented by the following general formula (I):

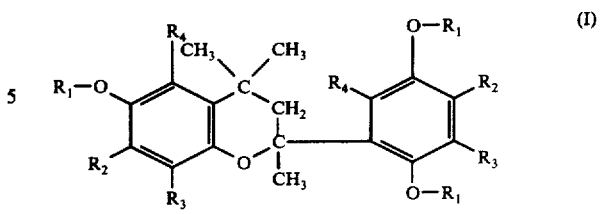

wherein $R_1$ represents a hydrogen atom or an —X—Y group in which X represents

(a carbonyl group) or

(a sulfonyl group); and Y represents a straight chain, branched chain or cyclic alkyl group having 1 to 20 carbon atoms which may be substituted with an acylamino group; an aryl group having 6 to 25 carbon atoms which may be unsubstituted or substituted with one or more of an alkyl group having 1 to 4 carbon atoms, an alkoxy group having 1 to 4 carbon atoms, a nitro group and a halogen atom; an aralkyl group having 7 to 10 carbon atoms; an alkoxy group containing a straight chain, branched chain or cyclic alkyl moiety having 1 to 20 carbon atoms; an aryloxy group having 6 to 26 carbon atoms which may be unsubstituted or substituted with one or more of an alkyl group having 1 to 4 carbon atoms, an alkoxy group having 1 to 4 carbon atoms, a nitro group and a halogen atom; an aralkoxy group having 7 to 10 carbon atoms; a straight chain, branched chain or cyclic alkoxycarbonyl group having 2 to 20 carbon atoms; an aryloxycarbonyl group having 7 to 26 carbon atoms which may be unsubstituted or substituted with one or more of an alkyl group having 1 to 4 carbon atoms, an alkoxy group having 1 to 4 carbon atoms, a nitro group and a halogen atom; or an aralkoxycarbonyl group having 8 to 11 carbon atoms; and $R_2$, $R_3$ and $R_4$, which may be the same or different, each represents a hydrogen atom; a straight chain, branched chain or cyclic alkyl group having 1 to 20 carbon atoms which may be unsubstituted or substituted with an acylamino group; a straight chain, branched chain or cyclic alkoxy group having 1 to 20 carbon atoms in the alkyl moiety thereof; an aryl group having 6 to 25 carbon atoms which may be unsubstituted or substituted with one or more of an alkyl group having 1 to 4 carbon atoms, an alkoxy group having 1 to 4 carbon atoms, an acylamino group, a nitro group and a halogen atom; an aryloxy group having 6 to 25 carbon atoms which may be unsubstituted or substituted with one or more of an alkyl group having 1 to 4 carbon atoms, an alkoxy group having 1 to 4 carbon atoms, an acylamino group, a nitro group and a halogen atom; an aralkyl group having 7 to 10 carbon atoms; an aralkoxy group having 7 to 10 carbon atoms; an alkenyl group having 2 to 20 carbon atoms; an alkenyloxy group having 2 to 20 carbon atoms; an acylamino group having 1 to 20 carbon atoms;

a halogen atom; an alkylthio group containing a straight chain, branched chain or cyclic alkyl moiety having 1 to 20 carbon atoms; an arylthio group having 6 to 25 carbon atoms which may be unsubstituted or substituted with one or more of an alkyl group having 1 to 4 carbon atoms, a carboxy group, an alkoxycarbonyl group having 2 to 5 carbon atoms and a nitro group; a diacylamino group having 2 to 40 carbon atoms; an unsubstituted or substituted acyl group having 1 to 20 carbon atoms; a sulfonamido group having up to 25 carbon atoms; an alkylamino group containing a straight chain, branched chain or cyclic alkyl moiety having 1 to 20 carbon atoms; an alkoxycarbonyl group containing a straight chain, branched chain or cyclic alkyl moiety having 1 to 20 carbon atoms; or an acyloxy group having 1 to 20 carbon atoms, provided that $R_2$, $R_3$ and $R_4$ do not simultaneously represent hydrogen atoms.

DETAILED DESCRIPTION OF THE INVENTION

With respect to —X—Y of $R_1$ in the general formula (I) Y specifically represents a straight chain, branched chain or cyclic alkyl group having 1 to 20 carbon atoms which may be substituted with an acylamino group (e.g., a methyl group, a tert-butyl group, a cyclohexyl group, a dodecyl group, an octadecyl group, a β-acetylaminopropyl group, etc.), an aryl group having 6 to 25 carbon atoms which may be unsubstituted or substituted with one or more of an alkyl group having 1 to 4 carbon atoms, an alkoxy group having 1 to 4 carbon atoms, a nitro group and a halogen atom (e.g., a phenyl group, a p-methylphenyl group, a p-methoxyphenyl group, an m-nitrophenyl group, an o-chlorophenyl group, an α-naphthyl group, etc.), an aralkyl group having 7 to 10 carbon atoms (e.g., a benzyl group, a phenethyl group, etc.), a straight chain, branched chain or cyclic alkoxy group having 1 to 20 carbon atoms (e.g., a methoxy group, a tert-butoxy group, a cyclohexyloxy group, a dodecyloxy group, an octadecyloxy group, etc.), an aryloxy group having 6 to 25 carbon atoms which may be unsubstituted or substituted with one or more of an alkyl group having 1 to 4 carbon atoms, an alkoxy group having 1 to 4 carbon atoms, a nitro group and a halogen atom (e.g., a phenoxy group, a p-methylphenoxy group, a p-methoxyphenoxy group, a p-isopropylphenoxy group, an m-nitrophenoxy group, an o-chlorophenoxy group, an α-naphthyloxy group, a β-naphthyloxy group, etc.), an aralkoxy group having 7 to 11 carbon atoms (e.g., a benzyloxy group, a phenethyloxy group, etc.), a straight chain, branched chain or cyclic alkyloxycarbonyl group having 2 to 20 carbon atoms (e.g., a methoxycarbonyl group, a tert-butoxycarbonyl group, a cyclohexyloxycarbonyl group, an octyloxycarbonyl group, etc.), an aryloxycarbonyl group having 7 to 26 carbon atoms which may be unsubstituted or substituted with one or more of an alkyl group having 1 to 4 carbon atoms, an alkoxy group having 1 to 4 carbon atoms, a nitro group and a halogen atom (e.g., a phenoxycarbonyl group, a p-methylphenoxycarbonyl group, a p-methoxyphenyloxycarbonyl group, an m-nitrophenoxycarbonyl group, an o-chlorophenoxycarbonyl group, etc.), or an aralkoxycarbonyl group having 8 to 11 carbon atoms (e.g., a benzyloxycarbonyl group, a phenethyloxycarbonyl group, etc.).

$R_2$, $R_3$ and $R_4$ in the general formula (I) each represents, specifically, a hydrogen atom, a straight chain, branched chain or cyclic alkyl group having 1 to 20 carbon atoms which may be unsubstituted or substituted with an acylamino group (e.g., a methyl group, a tert-butyl group, a cyclopentyl group, a cyclohexyl group, an octyl group, a dodecyl group, an octadecyl group, etc.), a straight chain, branched chain or cyclic alkoxy group having 1 to 20 carbon atoms (e.g., a methoxy group, a tert-butoxy group, a cyclohexloxy group, a dodecyloxy group, an octadecyloxy group, etc.), an aryl group having 6 to 25 carbon atoms which may be unsubstituted or substituted with one or more of an alkyl group having 1 to 4 carbon atoms, an alkoxy group having 1 to 4 carbon atoms, an acylamino group, a nitro group or a halogen atom (e.g., a phenyl group, a p-methylphenyl group, a p-methoxyphenyl group, a p-octanamidophenyl group, an o-chlorophenyl group, an o-methylphenyl group, an m-nitrophenyl group, an α-naphthyl group, etc.), an aryloxy group having 6 to 25 carbon atoms which may be unsubstituted or substituted with one or more of an alkyl group having 1 to 4 carbon atoms, an alkoxy group having 1 to 4 carbon atoms, an acylamino group, a nitro group or a halogen atom (e.g., a phenoxy group, an α-naphthoxy group, a p-methylphenoxy group, a p-methoxyphenoxy group, a p-capramidophenoxy group, an o-chlorophenoxy group, an m-nitrophenoxy group, etc.), an aralkyl group having 7 to 10 carbon atoms (e.g., a benzyl group, a phenethyl group, etc.), an aralkoxy group having 7 to 10 carbon atoms (e.g., a benzyloxy group, a phenethyloxy group, etc.), an alkenyl group having 2 to 20 carbon atoms (e.g., an allyl group, etc.), an alkenyloxy group having 2 to 20 carbon atoms (e.g., an allyloxy group, etc.), an acylamino group having 1 to 20 carbon atoms (e.g., an acetylamino group, a benzoylamino group, a capramido group, etc.), a halogen atom (e.g., a chlorine atom, etc.), a straight chain, branched chain or cyclic alkylthio group having 1 to 20 carbon atoms (e.g., a methylthio group, a tert-butylthio group, a hexylthio group, a cyclohexylthio group, an octadecylthio group, etc.), an arylthio group having 6 to 25 carbon atoms which may be unsubstituted or substituted with one or more of an alkyl group having 1 to 4 4 carbon atoms, a carboxy group, an alkoxycarbonyl group having 2 to 5 carbon atoms or a nitro group (e.g., a phenylthio group, a p-methylphenylthio group, an o-carboxyphenylthio group, an o-methylphenylthio group, an o-methoxycarbonylphenylthio group, an m-nitrophenylthio group, etc.), a diacylamino group having 2 to 40 carbon atoms (e.g., a succinimido group, a 3-hydantoinyl group, etc.), an unsubstituted or substituted acyl group having 1 to 20 carbon atoms (e.g., an acetyl group, a caproyl group, a p-methoxybenzoyl group, etc.), a sulfonamido group having 0 to 25 carbon atoms, a straight chain, branched chain or cyclic alkylamino group having 1 to 20 carbon atoms (e.g., an ethylamino group, a tert-butylamino group, a dioctylamino group, an octadecylamino group, etc.), a straight chain, branched chain or cyclic alkoxycarbonyl group having 2 to 20 carbon atoms (e.g. a methoxycarbonyl group a tert-butoxycarbonyl group, an octadecyloxycarbonyl group, etc.), or an acyloxy group having 1 to 20 carbon atoms (e.g., an acetoxy group, a caproyloxy group, a lauroyloxy group, a benzoyloxy group, etc.). In the above disclosure, the various aryl groups and aryl moieties can be either monocyclic or bicyclic aryl groups or moieties.

The compound represented by the general formula (I) is a good color image stabilizer.

Typical examples of these compounds are illustrated below, but the compounds which can be used in the present invention are not to be construed as being limited to these examples in any way.
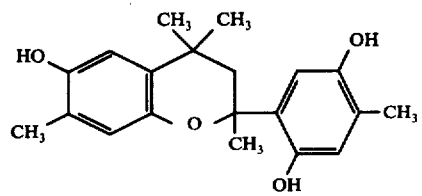 (1)
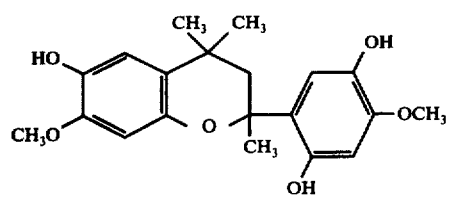 (2)
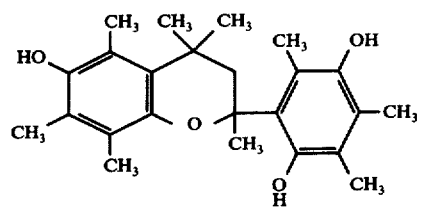 (3)
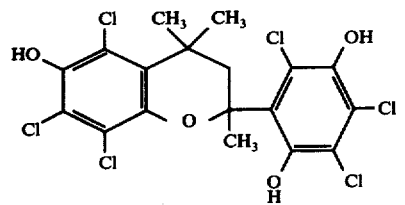 (4)
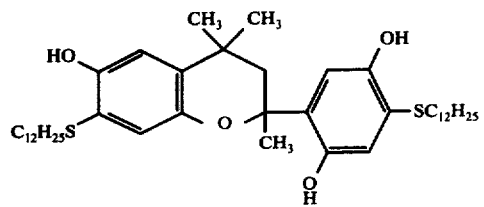 (5)
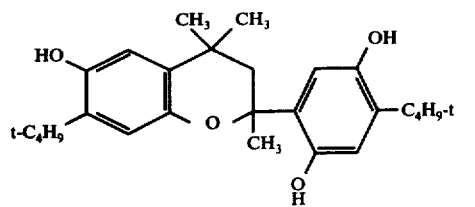 (6)
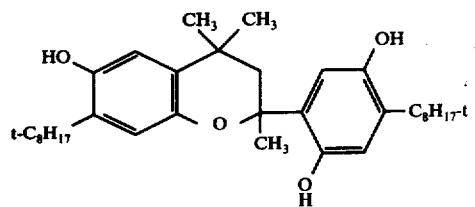 (7)
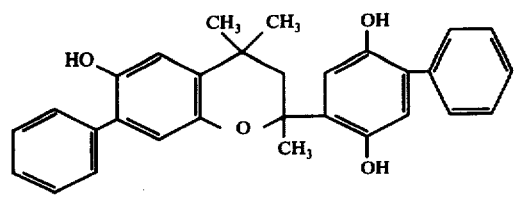 (8)

-continued
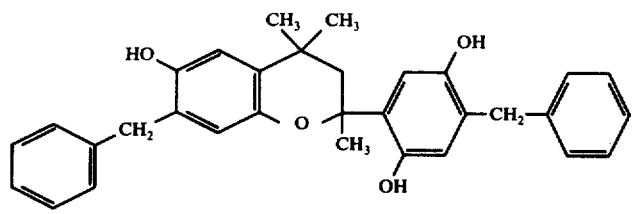 (9)
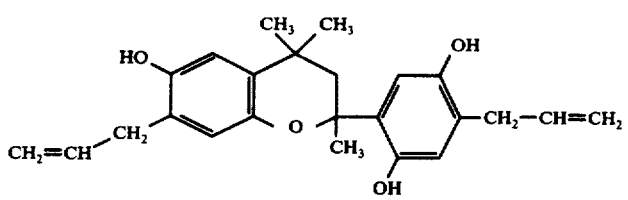 (10)
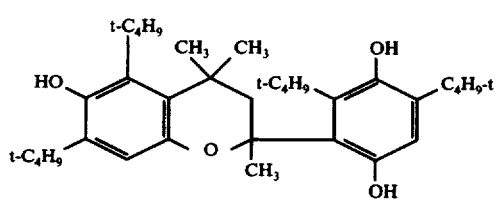 (11)
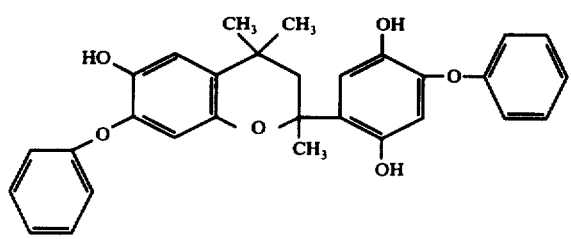 (12)
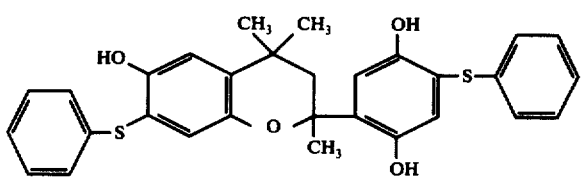 (13)
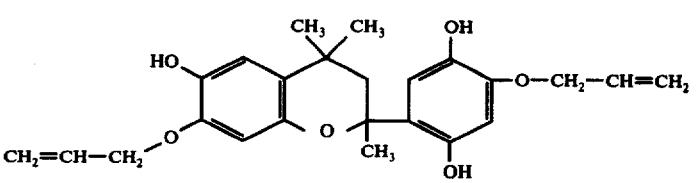 (14)
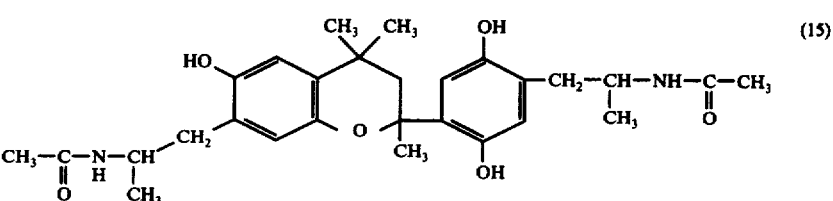 (15)
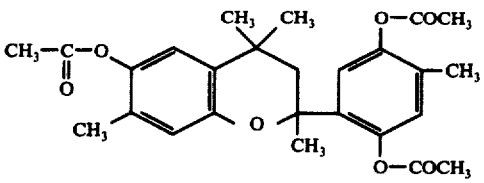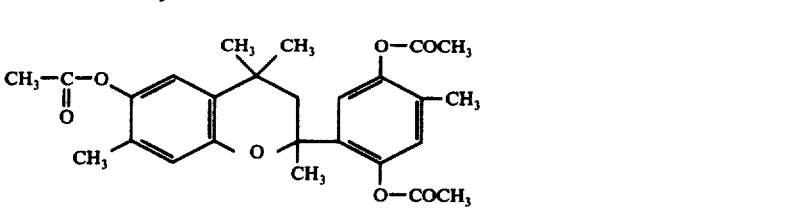 (16)

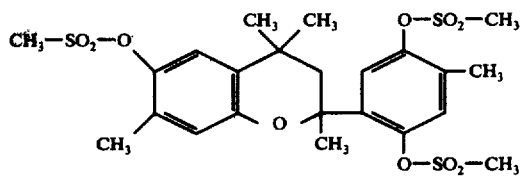 (17)
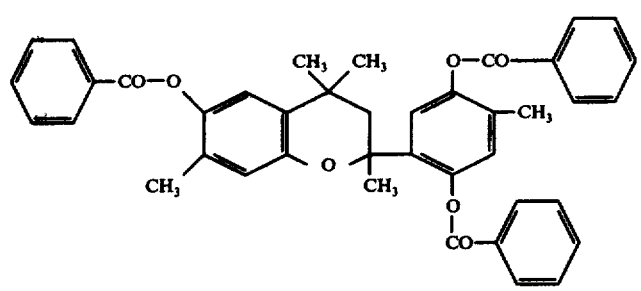 (18)
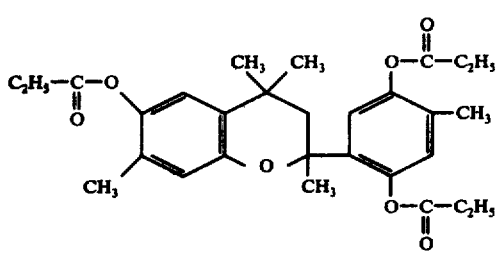 (19)
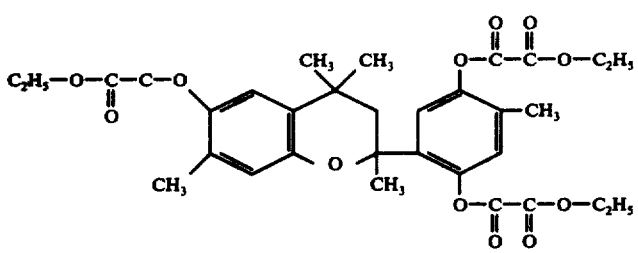 (20)
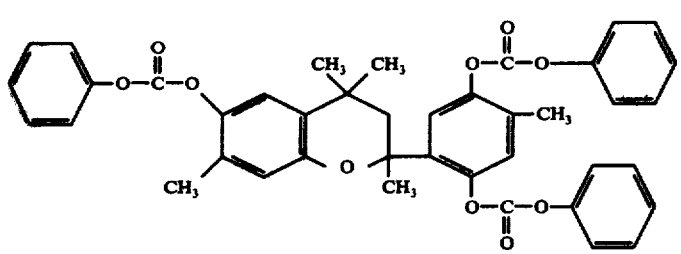 (21)
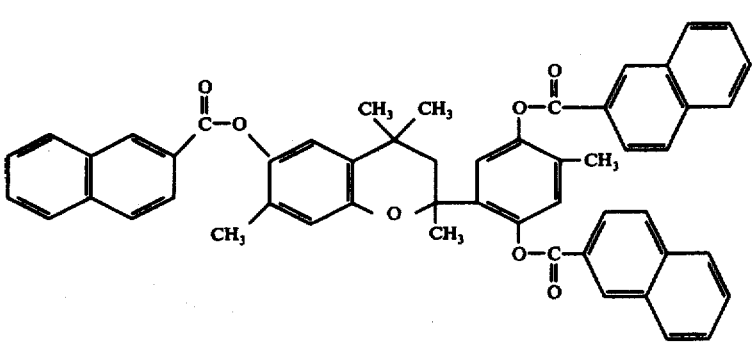 (22)

-continued

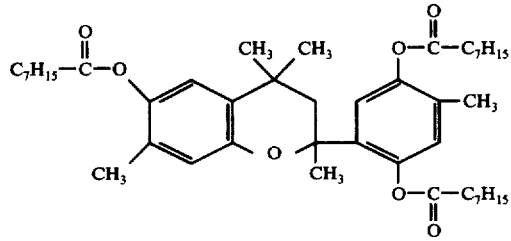

(23)

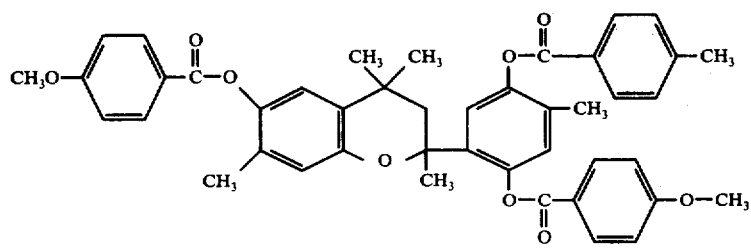

(24)

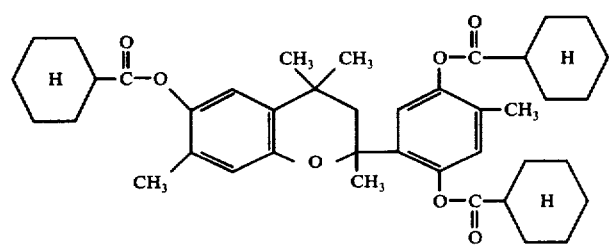

(25)

The synthesis of the compounds of the present invention is described below in detail.

Hydroquinones having substitutents corresponding to $R_2$, $R_3$ and $R_4$ in the general formula (I) and acetone are used as starting materials, and they are reacted with each other for more than about 1 day, preferably about 1 to 30 days at room temperature (about 20° – 30° C) using acetic acid and concentrated hydrochloric acid as catalysts, in the presence or absence of a solvent, with the compounds of the present invention being thus synthesized. Examples of suitable solvents which can be used in the synthesis of the compounds used in this invention include organic solvents such as benzene, toluene, methanol, ethanol, ethyl acetate, etc. A suitable molar ratio of the acetone to the hydroquinone starting material is about 0.5:1 to about 2:1. A suitable amount of the catalyst is about 0.5 to about 4 times by weight the amount of the hydroquinone starting material in the case of hydrochloric acid and about 0.5 to about 6 times by weight the amount of the hydroquinone starting material in the case of acetic acid (glacial).

Most of hydroquinones having substitutents corresponding to $R_2$, $R_3$ and $R_4$ in the general formula (I) are known compounds and are commercially available. 2-Alkylmercaptohydroquinones which are commercially available can be prepared by the addition reaction of p-benzoquinone and n-alkylmercaptans followed by reducing the resulting 2-n-alkylthio-p-benzoquinone as described in British Pat. No. 1,433,450.

a specific synthesis process is described below. Unless otherwise indicated, all parts, percents, ratios and the like are by weight.

SYNTHESIS EXAMPLE
Synthesis of Compound (1)

62 g of toluhydroquinone and 87 g of acetone were added to a mixed solution of 170 cc of concentrated hydrochloric acid (12N) and 300 cc of glacial acetic acid, and left for 16 days at 20°–30° C. The resulting crystals were recrystallized from ethanol to obtain 20 g of colorless needle-like crystals having a melting point of 190° C.

| Elemental Analysis | C (%) | H (%) |
|---|---|---|
| Calculated for $C_{20}H_{24}O_4$ (M.W. = 328): | 73.17 | 7.31 |
| Found: | 73.25 | 7.53 |

Illustrative couplers which can be used in the present invention include the following couplers. Examples of yellow couplers which can be used generally include open-chain ketomethylene compounds such as those described in, e.g., U.S. Pat. Nos. 3,341,331, 2,875,057, 3,551,155, German Pat. Application (OLS) No. 1,547,868, U.S. Pat. Nos. 3,265,506, 3,582,322, 3,725,072, German Patent Application (OLS) No. 2,162,899, U.S. Pat. Nos. 3,369,895, 3,408,194, German Patent Application (OLS) Nos. 2,057,941, 2,213,461, 2,219,917, 2,261,361, 2,263,875, etc.

Suitable magenta couplers which can be used include mainly 5-pyrazolone compounds. In addition, indazolone compounds and cyanoacetyl compounds can also be used. Examples of suitable magenta couplers are described in, e.g., U.S. Pat. Nos. 2,439,098, 2,600,788, 3,062,653, 3,558,319, Bristish Pat. No. 956,261, U.S. Pat. Nos. 3,582,322, 3,615,506, 3,519,429, 3,311,476, 3,419,391, 3,935,015, German Pat. Application (OLS) No. 2,424,467, German Pat. No. 1,810,464, Japanese Patent Publication No. 2,016/69, German Patent Application (OLS) No. 2,418,959, Japanese Pat. Application No. 118,540/75, U.S. Pat. No. 2,983,608, German Pat. Application (OLS) Nos. 2,532,225, 2,536,191, Japanese Pat. Application (OPI) No. 16,924/76, etc.

Phenol or naphthol derivatives are predominantly used as cyan couplers. Suitable examples of cyan couplers are described in, e.g., U.S. Pat. Nos. 2,369,929, 2,474,293, 2,698,794, 2,895,826, 3,311,476, 3,458,315, 3,560,212, 3,582,322, 3,591,383, 3,386,301, 2,434,272, 2,706,684, 3,034,892, 3,583,971, German Patent Application (OLS) No. 2,163,811, Japanese Patent Publication No. 28,836/70, Japanese Patent Application No. 33,238/73, etc.

In addition, couplers capable of releasing a development inhibitor upon color reaction (so-called DIR couplers) or compounds capable of releasing a development inhibiting compound may also be employed. Examples of these couplers are described in, e.g., U.S. Pat. Nos. 3,148,062, 3,227,554, 3,253,924, 3,617,291, 3,622,328, 3,705,201, British Pat. No. 1,201,110, U.S. Pat. Nos. 3,297,445, 3,379,529, 3,639,417, etc.

Colored couplers can also be used in the present invention, and examples are illustrated in U.S. Pat. Nos. 2,434,272, 3,476,564, 3,476,560, Japanese Pat. Application No. 45,971/73, U.S. Pat. Nos. 3,034,892, 3,386,301, 2,434,272, 3,148,062, 3,227,554, 3,701,783, 3,617,291, etc.

The magenta couplers which can be used in the present invention can be selected from a wide range of conventional magenta couplers. Magenta couplers providing particularly advantageous effects are represented by the following general formulae (II) and (III):

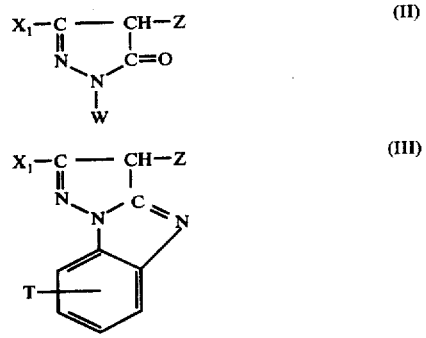

Wherein W represents a hydrogen atom or a group with 1 to 35 carbon atoms, preferably 1 to 22 carbon atoms which includes a straight chain or branched chain alkyl group (for example, a methyl, isopropyl, tert-butyl, hexyl, dodecyl group, etc.), an alkenyl group (for example, an allyl group, etc.), a cycloalkyl group (for example, a cyclopentyl, cyclohexyl, norbornyl group, etc.), an aralkyl group (for example, a benzyl, β-phenylethyl group, etc.) and a cycloalkenyl group (for example, a cyclopentenyl, cyclohexenyl - etc.); which groups can be substituted with one or more substituents selected from a halogen atom or a nitro group, a cyano group, a monoaryl group (preferably having 6 to 12 carbon atoms), an alkoxy group (preferably having 1 to 20 carbon atoms), a monoaryloxy group (preferably having 6 to 12 carbon atoms), a carboxy group, an alkylcarbonyl group (where the alkyl moiety preferably has 1 to 20 carbon atoms), a monoarylcarbonyl group (where the aryl moiety preferably has 6 to 12 carbon atoms), an alkoxycarbonyl group (where the alkoxy moiety preferably has 1 to 20 carbon atoms), a monoaryloxycarbonyl group (where the aryloxy moiety preferably has 6 to 12 carbon atoms), a sulfo group, an acyloxy group (preferably having 2 to 20 carbon atoms), a sulfamoyl group, a carbamoyl group, an acylamino group (preferably having 2 to 20 carbon atoms), an imido group having 3 to 20 carbon atoms (for example, succinimido, maleimido, phthalimido, glutarimido, heptadecanoylaminosuccinimido, adipic acid imido and 3-(2,4-di-t-pentylphenyloxyacetamido)phthalimido etc.), a ureido group, a thioureido group, a urethane group, a thiourethane group, a sulfonamido group, a heterocyclic group (preferably a 5-membered or 6-membered heterocyclic group which can be condensed with an aromatic ring such as a benzene ring, etc., for example, N-pyrrolidinyl and N-morpholino, etc.), an arylsulfonyloxy group (where the aryl moiety preferably has 6 to 12 carbon atoms and can comprise a single or condensed ring), an alkylsulfonyloxy group (preferably having 1 to 20 carbon atoms), an arylsulfonyl group (where the aryl moiety preferably has 6 to 12 carbon atoms and can comprise a single or condensed ring), an alkylsulfonyl group (preferably having 1 to 20 carbon atoms), an arylthio group (where the aryl moiety preferably has 6 to 12 carbon atoms and can comprise a single or condensed ring), an alkylthio group (preferably having 1 to 20 carbon atoms), an alkylsulfinyl group (preferably having 1 to 20 carbon atoms), an arylsulfinyl group (where the aryl moiety preferably has 6 to 12 carbon atoms and can comprise a single or condensed ring), an alkylamino group (preferably having 1 to 20 carbon atoms), a dialkylamino group (preferably having 2 to 24 carbon atoms), an anilino group, an N-arylanilino group (where the aryl moiety preferably has 6 to 12 carbon atoms and can comprise a single or condensed ring), an N-alkylanilino group (where the alkyl moiety preferably has 1 to 20 carbon atoms), an N-acylanilino group (where the acyl moiety preferably has 2 to 20 carbon atoms), a hydroxy group and a mercapto group; or W represents an aryl group (preferably an aryl group having 6 to 12 carbon atoms and comprises a single or condensed ring, for example, a phenyl, α- or β-naphthyl group, etc.) and an aryl group having 1 to 5 substituents selected from a halogen atom or an alkyl group (preferably having 1 to 20 carbon atoms), an alkenyl group (preferably having 1 to 20 carbon atoms), a monocycloalkyl group (preferably having 5 to 7 carbon atoms), an aralkyl group (preferably having 7 to 10 carbon atoms, where the aryl moiety preferably has a single ring), a monocycloalkenyl group (preferably having 5 to 7 carbon atoms), a nitro group, a cyano group, a mono- or polycyclic aryl group (preferably having 6 to 12 carbon atoms), an alkoxy group (preferably having 1 to 20 carbon atoms), a mono- or polycyclic aryloxy group (preferably having 6 to 12 carbon atoms), a carboxy group, an alkylcarbonyl group (where the alkyl moiety preferably has 1 to 20 carbon atoms), an arylcarbonyl group (where the aryl moiety preferably has 6 to 12 carbon atoms and comprises a single or condensed ring), an alkoxycarbonyl group (where the alkoxy moiety preferably has 1 to 20 carbon atoms), an aryloxycarbonyl group (where the aryl moiety preferably has 6 to 12 carbon atoms and comprises a single or condensed ring), a sulfo group, an acyloxy group (preferably having 2 to 20 carbon atoms), a sulfamoyl group, a carbamoyl group, an acylamino group (preferably having 2 to 20 carbon atoms), an imido group (preferably having 3 to 20 carbon atoms), a ureido group, a thiouredio group, a urethane group, a thiourethane group, a sulfonamido group, a heterocyclic group (for example, a 5-membered or 6-membered heterocyclic group which can be condensed with an aromatic ring such as benzene, etc., and containing N, O and/or S as a hetero atom, for example, pyrrolidinyl, piperidyl, morpholino, pyridyl, quinolyl, furyl, benzothiazolyl, oxazolyl and imidazolyl, etc.), an arylsulfonyloxy group (where the aryl moiety preferably has 6 to 12 carbon atoms and comprises a single or condensed ring), an alkylsulfonyloxy group (preferably having 1 to 20 carbon atoms), an arylsulfonyl group (where the aryl moiety preferably has 6 to 12 carbon atoms and comprises a single or condensed ring), an alkylsulfonyl group (preferably having 1 to 20 carbon atoms), an arylthio group (where the aryl moiety preferably has 6 to 12 carbon atoms and comprises a single or condensed ring), an alkylthio group (preferably having 1 to 20 carbon atoms), an alkylsulfinyl group (preferably having 1 to 20 carbon atoms), an arylsulfinyl group (where the aryl moiety preferably has 6 to 12 carbon atoms and comprises a single or condensed ring), an alkylamino group (preferably having 1 to 20 carbon atoms), a dialkylamino group (preferably having 2 to 24 carbon atoms), an anilino group, an N-alkylanilino group (where the alkyl moiety preferably has 1 to 20 carbon atoms), an N-arylanilino group (where the aryl moiety preferably has 6 to 12 carbon atoms and comprises a single or condensed ring), an N-acylanilino group (where the acyl moiety preferably has 2 to 20 carbon atoms), a hydroxy group and a mercapto group. A phenyl group in which at least one of the ortho-position is substituted with an alkyl group preferably having 1 to 8 carbon atoms, an alkoxy group preferably having 1 to 8 carbon atoms or a halogen atom is particularly useful for W, since, when the coupler remains in a color photographic material after development, less printout by the action of light or heat occur.

Furthermore, W represents a heterocyclic group (for example, a 5-membered or 6-membered heterocyclic group or a condensed heterocyclic group, for example, condensed with a benzene ring or a naphthylene ring, containing a nitrogen atom, an oxygen atom or a sulfur atom as a hetero atom (for ease of production, the balance of the atoms being carbon atoms) such as pyridyl, quinolyl, furyl, benzothiazolyl, oxazolyl, imidazolyl, naphthoxazolyl group, etc.) or a substituted heterocyclic group with one or more substituents above-described for the aryl group for W.

Furthermore, W represents an acyl group (preferably having 2 to 20 carbon atoms), a thioacyl group (preferably having 2 to 20 carbon atoms), an alkylsulfonyl group (preferably having 1 to 20 carbon atoms), an arylsulfonyl group (preferably having 6 to 12 carbon atoms in the aryl moiety, the aryl moiety comprising a single or condensed ring), an alkylsulfinyl group (preferably having 1 to 20 carbon atoms), an arylsulfinyl group (preferably having 6 to 12 carbon atoms in the aryl moiety, the aryl moiety comprising a single or condensed ring), a carbamoyl group or a thiocarbamoyl group.

In the formulae, $X_1$ represents a hydrogen atom or a group having 1 to 35 carbon atoms, preferably 1 to 22 carbon atoms, which includes a straight chain or branched chain alkyl group, an alkenyl group, a cycloalkyl group, an aralkyl group and a cycloalkenyl group, which groups can have one or more substituents above described for W;

Further, $X_1$ represents an aryl group preferably having 6 to 12 carbon atoms, and comprises a single or condensed ring, or a heterocyclic group which can be substituted with one or more substituents as described for W, where the heterocyclic group preferably is a 5-membered or 6-membered heterocyclic group or a condensed heterocyclic group containing a nitrogen atom, an oxygen atom or a sulfur atom as a hetero atom;

Furthermore, $X_1$ represents an alkoxycarbonyl group (wherein the alkoxy moiety preferably has 1 to 20 carbon atoms, for example, a methoxycarbonyl, ethoxycarbonyl, stearyloxycarbonyl group, etc.), an aryloxycarbonyl group (wherein the aryl moiety preferably has 6 to 12 carbon atoms and comprises a single or condensed ring, for example, a phenoxycarbonyl, α- or β-naphthoxycarbonyl group, etc.), an aralkyloxycarbonyl group (wherein the aralkyloxy moiety preferably has 7 to 10 carbon atoms and the aryl moiety comprises a single or condensed ring, for example, a benzyloxycarbonyl group, etc.), an alkoxy group (preferably having 1 to 20 carbon atoms, for example, a methoxy, ethoxy, dodecyloxy group, etc.), an aryloxy group (wherein the aryl moiety preferably has 6 to 12 carbon atoms and comprises a single or condensed ring, for example, a phenoxy, tolyloxy group, etc.), an alkylthio group (preferably having 1 to 20 carbon atoms, for example, an ethylthio, dodecylthio group, etc.), an arylthio group (wherein the aryl moiety preferably has 6 to 12 carbon atoms and comprises a single or condensed ring, for example, a phenylthio, α-naphthylthio group, etc,), a carboxy group, an acylamino group (preferably having 2 to 20 carbon atoms, for example, an acetamido, 3-[(2,4-di-tert-amylphenoxy)acetamido]-benzamido group, etc.), an imido group, preferably having 3 to 20 carbon atoms, an N-alkylacylamino group (wherein the alkyl moiety preferably has 1 to 20 carbon atoms, for example, an N-methylpropionamido group, etc.), an N-arylacylamino group (wherein the aryl moiety preferably has 6 to 12 carbon atoms and comprises a single or condensed ring, for example, an N-phenylacetamido group, etc.), a ureido group (for example, a ureido, N-arylureido (where the aryl moiety preferably has 6 to 12 carbon atoms and comprises a single or condensed ring) or N-alkylureido group (where the alkyl moiety preferably has 1 to 20 carbon atoms), etc.), a thioureido group (for example, a thioureido, N-arylthioureido (where the aryl moiety preferably has 6 to 12 carbon atoms and comprises a single or condensed ring), or N-alkylthioureido group (where the alkyl moiety preferably has 1 to 20 carbon atoms), etc.), a urethane group, a thiourethane group, an anilino group (for example, a phenylamino, N-alkylanilino (where the alkyl moiety preferably has 1 to 20 carbon atoms), N-arylanilino (where the aryl moiety preferably has 6 to 12 carbon atoms and comprises a single or condensed ring), N-acylanilino (where the acyl moiety preferably has 2 to 20 carbon atoms), or 2-chloro-5-tetradecanamidoanilino group, etc.), an alkyl-amino group (preferably having 1 to 20 carbon atoms, for example, an N-butylamino, N,N-dialkylamino or cycloalkylamino group (where the cycloalkyl moiety preferably has 5 to 7 carbon atoms and comprises a single ring, etc.)), a cycloamino group (preferably having 4 to 9 carbon atoms and comprises a single or condensed ring, for example, a piperidino, pyrrolidino group, etc.), an alkylcarbonyl group (wherein the alkyl moiety preferably has 1 to 20 carbon atoms, for example, a methylcarbonyl group, etc.), an arylcarbonyl group (wherein the aryl moiety preferably has 6 to 12 carbon atoms and comprises a single or condensed ring, for example, a phenylcarbonyl group, etc.), a sulfonamido group (for example, an alkylsulfonamido (where the alkyl moiety preferably has 1 to 20 carbon atoms) or arylsulfonamido group (where the aryl moiety preferably has 6 to 12 carbon atoms and comprises a single or condensed ring, etc.), a carbamoyl group (for example, an N-alkylcarbamoyl (where the alkyl moiety preferably has 1 to 20 carbon atoms), N,N-dialkylcarbamoyl (where the alkyl moiety preferably has 1 to 20 carbon atoms), N-alkyl-N-arylcarbamoyl (where the alkyl moiety preferably has 1 to 20 carbon atoms, and the aryl moiety preferably has 6 to 12 carbon atoms and comprises a single or condensed ring), N-arylcarbamoyl (where the aryl moiety preferably has 6 to 12 carbon atoms and comprises a single or condensed ring), or N,N-diarylcarbamoyl group (where the aryl moiety preferably has 6 to 12 carbon atoms and comprises a single or condensed ring), etc.), a sulfamoyl group (for example, an N-alkylsulfamoyl (where the alkyl moiety preferably has 1 to 20 carbon atoms), N,N-dialkylsulfamoyl (where the alkyl moiety preferably has 1 to 24 carbon atoms), N-arylsulfamoyl (where the aryl moiety preferably has 6 to 12 carbon atoms and comprises a single or condensed ring, N-alkyl-N-arylsulfamoyl (where the alkyl moiety preferably has 1 to 20 carbon atoms, and the aryl moiety preferably has 6 to 12 carbon atoms and comprises a single or condensed ring) or N,N-diarylsulfamoyl group (where the aryl moiety preferably has 6 to 12 carbon atoms and comprises a single or condensed ring), etc.), a guanidino group (for example, an N-alkylguanidino (where the alkyl moiety preferably has 1 to 20 carbon atoms) or N-arylguanidino group (where the aryl moiety preferably has 6 to 12 carbon atoms and comprises a single or condensed ring), etc.), a cyano group, an acyloxy group (for example, a tetradecanoyloxy group, etc.), a sulfonyloxy group (for example, an alkylsulfonyloxy (preferably having 1 to 20 carbon atoms), arylsulfonyloxy (preferably having 6 to 12 carbon atoms and comprising a single or condensed ring) or an aralkylsulfonyloxy group (preferably having 7 to 12 carbon atoms), for example, benzenesulfonyloxy, dodecylsulfonyloxy group, etc.), a hydroxy group, a mercapto group, a halogen atom or a sulfo group;

T represents a hydrogen atom or a group having 1 to 35 carbon atoms, preferably 1 to 22 carbon atoms, which includes a straight chain or branched chain alkyl group, an alkenyl group, a cycloalkyl group, an aralkyl group, and a cycloalkenyl group, which can be substituted with one or more substituents as described for W;

Further, T represents an aryl group preferably having 6 to 12 carbon atoms and comprises a single or condensed ring, or a heterocyclic group which can be substituted with one or more substituents as described for W, where the heterocyclic group preferably is a 5-membered or 6-membered heterocyclic group or a condensed heterocyclic group containing a nitrogen atom, an oxygen atom or a sulfur atom as a hetero atom.

Also T can represent a halogen atom, a cyano group, an alkoxy group (preferably having 1 to 20 carbon atoms), an aryloxy group (preferably having 6 to 12 carbon atoms and comprising a single or condensed ring), a carboxy group, an alkoxycarbonyl group (preferably having an alkoxy moiety with 1 to 20 carbon atoms), an aryloxycarbonyl group (preferably having an aryl moiety with 6 to 12 carbon atoms and comprising a single or condensed ring), an acyloxy group (preferably having 2 to 20 carbon atoms), an alkylcarbonyl group (preferably having an alkyl moiety with 1 to 20 carbon atoms), an arylcarbonyl group (preferably having an aryl moiety with 6 to 12 carbon atoms and comprising a single or condensed ring), an alkylthiocarbonyl group (preferably having an alkyl moiety with 1 to 20 carbon atoms), a sulfo group, a sulfamoyl group, a carbamoyl group, an arylthio-carbonyl group (preferably having an aryl moiety with 6 to 12 carbon atoms and comprising a single or condensed ring), an acylamino group (preferably having 2 to 20 carbon atoms). an imido group (preferably having 3 to 20 carbon atoms), a ureido group, a thioureido group, a urethane group, a thiourethane group, a sulfonamido group, an alkylsulfonyloxy group (preferably having 1 to 20 carbon atoms), an arylsulfonyloxy group (preferabyl having an aryl moiety with 6 to 12 carbon atoms and comprising a single or condensed ring), an arylsulfonyl group (preferably having an aryl moiety with 6 to 12 carbon atoms and comprising a single or condensed ring), an alkylsulfonyl group (preferably having 1 to 20 carbon atoms), an arylthio group (preferably having an aryl moiety with 6 to 12 carbon atoms and comprising a single or condensed ring), an alkylthio group (preferably having 1 to 20 carbon atoms), an alkylsulfinyl group (preferably having 1 to 20 carbon atoms), an arylsulfinyl group (preferably having an aryl moiety with 6 to 12 carbon atoms and comprising a single or condensed ring), an alkylamino group (preferably having 1 to 20 carbon atoms), a dialkylamino group (preferably having 2 to 24 carbon atoms), an anilino group, an N-arylanilino group (preferably having an aryl moiety with 6 to 12 carbon atoms and comprising a single or condensed ring), an N-alkylanilino group (preferably having an alkyl moiety with 1 to 20 carbon atoms), an N-acylanilino group (preferably having an acyl moiety with 2 to 20 carbon atoms), a hydroxy group or a mercapto group.

Z preferably represents a hydrogen atom or or a coupling-off group bonded to the coupling position through an oxygen atom, a nitrogen atom or a sulfur atom.

Z more preferably represents a hydrogen atom or a coupling-off group in which an alkyl group preferably having 1 to 20 carbon atoms (which includes a straight chain or branched chain alkyl group), an aryl group (preferably having 6 to 12 carbon atoms and comprising a single or condensed ring), a sulfonyl group, a sulfinyl group, a carbonyl group, a phosphoric acid group, a thiocarbonyl group, or a heterocyclic group (where the heterocyclic group preferably is a 5-membered or 6-membered heterocyclic group or a condensed heterocyclic group containing a nitrogen atom, an oxygen atom or a sulfur atom as a hetero atom) is bonded to an oxygen atom, a nitrogen atom or a sulfur atom which is directly bonded to the coupling position of a coupling-off group forming a 5- or 6-membered nitrogen-containing ring (the maximum number of nitrogen atoms being 4) in which the nitrogen atom is directly bonded to the coupling position, and the heterocyclic ring preferably has 1 to 14 carbon atoms (for example, tetrazolyl, benztriazole-1-yl, benztriazole-2-yl, 1-benzimidazolyl, pyrrolidinyl, piperidyl, morpholinyl, etc.).

Preferred coupling-off groups for Z which are bonded to the coupling position through an oxygen atom include, for example, an acyloxy group (preferably having 2 to 20 carbon atoms), an aryloxy group (preferably having 6 to 12 carbon atoms and comprising a single or condensed ring), an alkoxy group (preferably having 1 to 20 carbon atoms), an alkoxycarbonyloxy group (wherein the alkoxy moiety preferably has 1 to 20 carbon atoms), an alkoxyalkyl group (wherein the alkoxy moiety preferably has 1 to 20 carbon atoms), a heterocyclic oxy group (preferably having a 5- or 6-membered heterocyclic group or a condensed heterocyclic group, for example, 4 -pyridyloxy and 2-quinolyloxy, etc.), a phosphate group, a thiophosphate group, a carbamoyloxy group, a thiocarbamoyloxy group, an oxamoyloxy group, a thiooxazoyloxy group, and the like.

Preferred coupling-off groups for Z which are bonded to the coupling position through a sulfur atom include, for example, a thiocyano group, an alkylthio group (preferably having 1 to 20 carbon atoms), an arylthio group (wherein the aryl moiety preferably has 6 to 12 carbon atoms and comprises a single or condensed ring), a heterocyclic thio group (preferably a heterocyclic thio group having a 5- or 6-membered heterocyclic group or a condensed heterocyclic group, for example, 5-tetrazolylthio, 2-benzimidazolylthio, 2-benzthiazolylthio, 2-thiazolylthio, 1,2,4-triazol-3-ylthio and 2-benzoxazolylthio, etc.), an alkylsulfinyl group (preferably having 1 to 20 carbon atoms), an arylsulfinyl group (where the aryl moiety preferably has 6 to 12 carbon atoms and comprises a single or condensed ring), a heterocyclic sulfinyl group (preferably a heterocyclic sulfinyl group having a 5- or 6-membered heterocyclic group or a condensed heterocyclic group, for example, 2-benzimidazolylsulfinyl, 2-thiazolylsulfinyl, 2-benzothiazolylsulfinyl and 2-benzoxazolylsulfinyl, etc.), an alkylsulfonyl group (preferably having 1 to 20 carbon atoms), an arylsulfonyl group (wherein the aryl moiety preferably has 6 to 12 carbon atoms and comprises a single or condensed ring), a heterocyclic sulfonyl group (preferably a heterocyclic sulfonyl group having a 5- or 6-membered heterocyclic group or a condensed heterocyclic group, for example, 2-benzimidazolylsulfonyl, 2-thiazolylsulfonyl, 2-benzthiazolylsulfonyl and 2-benzoxazolylsulfonyl, etc.), a sulfo group, an alkylsulfonylthio group (preferably having 1 to 20 carbon atoms), an arylsulfonylthio group (wherein the aryl moiety preferably has 6 to 12 carbon atoms and comprises a single or condensed ring), a disulfido group, a sulfido group, a thiocarbamate group, a dithiocarbamate group, a thiocarbamate group, a dithiocarbonate group, and the like.

Preferred coupling-off groups for Z which are bonded to the coupling position through a nitrogen atom include, for example, an acylamino group (preferably having 2 to 20 carbon atoms), an imido group (preferably having 3 to 20 carbon atoms), a sulfonamido group, a sulfinamido group, an alkylamino group (preferably having 1 to 20 carbon atoms), an arylamino group (wherein the aryl moiety preferably has 6 to 12 carbon atoms and comprises a single or condensed ring), a ureido group, a thioureido group, a phosphoric amido group, a urethane group, a thioacylamino group (preferably having 2 to 20 carbon atoms), an isocyanate group, and the like, and a nitrogen containing 5- and 6-membered heterocyclic ring (containing a maximum of 4 nitrogen atoms, for example, a cycloamino ring such as pyrrolidine, morpholine, piperazine, indoline, piperidine, etc., a cyclic diacylamino ring such as phthalimide, succinimide, saccharin, oxazolidione, thiohydantoin, hydantoin, etc., a cycloamido ring such as pyridone, oxazolidone, phthalide, valerolactam, etc., an aromatic cycloamino ring such as imidazole, pyrrole, benzotriazole, etc.), and the like.

Examples of magenta couplers useful in the present invention are illustrated below. However, the invention is not to be construed as being limited to these specific examples.

Cp-1

1-(2,4,6-Trichlorophenyl)-3-{3-(2,4-di-tert-amylphenoxy)butyramido]benzamido}-5-oxo-2-pyrazoline Cp-2

1-(2,4,6-Trichlorophenyl)-3-[3-(α-ethoxycarbonyloctadecanamido)benzamido]-5-oxo-2-pyrazoline Cp-3

1-(2,4-Dimethyl-6-chlorophenyl)-3-{3-[(2,4-di-tert-amylphenoxy)acetamido]benzamido}-5-oxo-2-pyrazoline Cp-4

1-(2,4,6-Trichlorophenyl)-3-{3-[(2,4-di-tert-amylphenoxy)acetamido]benzamido}-5-oxo-2-pyrazoline-4-yl-benzylcarbonate Cp-5

1-[4-(4-tert-amylphenoxy)phenyl]-3-[α-(4-tert-amylphenoxy)propionamido]-5-oxo-2-pyrazoline Cp-6

1-(2,4,6-Trichlorophenyl)-3-(2-chloro-5-tetradecanamido)anilino-5-oxo-2-pyrazoline Cp-7

1-(2,6-Dichloro-4-methoxyphenyl)-3-{2-chloro-5-[α-(2,4-di-tert-amylphenoxy)butyramido]anilino}-4-phenylthio-5-oxo-2-pyrazoline Cp-8

1-(2,6-Dichloro-4-methoxyphenyl)-3-{3-[α-(3-n-pentadecylphenoxy)butyramido]benzamido}-5-oxo-2-pyrazoline Cp-9

1-(2,4-Dimethyl-6-chlorophenyl)-3-{3-[β-dodecyloxycarbonyl)propionamido]benzamido}-5-oxo-2-pyrazoline Cp-10

1-(2,4,6-Trichlorophenyl)-3-{2-chloro-5-[α-(4-methoxyphenoxy)tetradecanamido]anilino}-5-oxo-2-pyrazoline Cp-11

1-(2,4,6-Trichlorophenyl)-3-{3-[α-(2,4-di-tert-amylphenoxy)butyramido]benzamido-4-imidazolyl}-5-oxo-2-pyrazoline Cp-12

1-(2,4,6-Trichlorophenyl)-3-{2-chloro-5-[α-(3,5-di-tert-butyl-4-hydroxyphenoxy)tetradecanamido]anilino}-5-oxo-2-pyrazoline Cp-13

1-(2,6-Dichloro-4-methylphenyl)-3-{3-[(3-n-pentadecylphenoxy)acetamido]benzamido}-5-oxo-2-pyrazoline Cp-14

1-(2,4,6-Trichlorophenyl)-3-{γ-[2-hydroxy-3-(2-benzotriazolyl)-5-n-pentylphenyl]butyramido}-5-oxo-2-pyrazoline Cp-15

1-(2,4,6-Trichlorophenyl)-3-{2-chloro-5-[β-dodecyloxycarbonyl)ethylcarbonyl]anilino}-5-oxo-2-pyrazoline Cp-16

1-(2,4,6-Trichlorophenyl)-3-[3-dodecylureido)-benzamido]-5-oxo-2-pyrazoline

Cp-17

1-(2,4,6-Trichlorophenyl)-3-[α-(2,4-di-tert-amylphenoxy)butyramido]-4-pentafluorobenzamido-5-oxo-2-pyrazoline Cp-18

1-(2,6-Dichloro-4-tetradecyloxycarbonylphenyl)-3-(2-chloro-5-methoxycarbonylanilino)-5-oxo-2-pyrazoline Cp-19

1-(2,4,6-Trichlorophenyl)-3-(α-carboxymethyl-n-2-eicosenamido)benzamido-5-oxo-2-pyrazoline Cp-20

1-{4-[(2,4-Di-tert-amylphenoxy)acetamido]phenyl}-3-(3-acetamido-benzamido)-5-oxo-2-pyrazoline Cp-21

1-(2,4,6-Trichlorophenyl)-3-{3-[(2-tetradecyl-4-chlorophenoxy)acetamido]benzamido}-5-oxo-2-pyrazoline Cp-22

1-(2,4-Dimethyl-6-chlorophenyl)-3-{3-[α-(2,4-di-tert-amylphenoxy)butyramido]phenylureido}-5-oxo-2-pyrazoline Cp-23

1-(2,4,6-Trichlorophenyl)-3-{3-[α-(2,4-di-tert-amylphenoxy)butyramido]benzamido}-4-phenylsulfonamido-5-oxo-2-pyrazoline Cp-24

1-(2,4,6-Trichlorophenyl)-3-{2-chloro-5-[α-(3-tert-butyl-4-hydroxyphenoxy)tetradecanamido]anilino}-5-oxo-2-pyrazoline Cp-25

1-(2,4,6-Trichlorophenyl)-3-{2-chloro-5-[β-(2,2-dimethyl-6-hydroxy-7-tert-octyl-4-chromanyl)propionamido]-anilino}-5-oxo-2-pyrazoline Cp-26

2-{3-[α-(2,4-Di-tert-amylphenoxy)butyramido]-benzamido}-7-chloropyrazolo-[1,5a]-benzimidazole Cp-27

1-(2,4,6-Trichlorophenyl)-3-{[2-chloro-5-(3,5-dicarboxyphenoxy-acetamido)]anilino}-4-[(4-N-methyl-N-octadecylsulfamoyl)phenoxy]-5-oxo-2-pyrazoline Cp-28

1-(2-Methylphenyl)-3-(3,5-dicarboxyanilino)-4-(3-octadecylcarbamoylphenylthio)-5-oxo-2-pyrazoline Cp-29

1-(2,6-Dichloro-4-methoxycarbonylphenyl)-3-{3-[α-(3-pentadecylphenoxy)butyramido]benzamido}-5-oxo-2-pyrazoline Cp-30

1-(2,4,6-Trichlorophenyl)-3-{3-[(2,4-di-tertamylphenoxy)acetamido]benzamido}-4-(4-methoxyphenylazo)-5-oxo-2-pyrazoline Cp-31

1-(2,4,6-Trichlorophenyl)-3-(2-chloro-5-tetradecanamidoanilino)-4-(3-methyl-4-hydroxyphenylazo)-5-oxo-2-pyrazoline Cp-32

1-(2,4,6-Trichlorophenyl)-3-{2-chloro-5-[3-(2-dodecylcarbamoylethylthio)propanamido]anilino}-5-oxo-2-pyrazoline The color image stabilizer of the general formula (I) used in the present invention is suitably employed in an amount of about 0.5 to about 200% by weight, preferably 2 to 150% by weight, based on the weight of the couplers, although the amount thereof will vary some depending upon the kind of couplers employed. A suitable coating amount of the coupler ranges from about $5 \times 10^{-3}$ to about $1 \times 10^{-4}$ mol/m$^2$, preferably $3.5 \times 10^{-3}$ to $3 \times 10^{-4}$ mol/m$^2$ of the support. A suitable coating amount of silver ranges from about $3 \times 10^{-2}$ to about $2 \times 10^{-4}$ mol/m$^2$, preferably $2 \times 10^{-2}$ to $6 \times 10^{-4}$ mol/m$^2$ of the support.

If the compound of the general formula (I) is employed in an amount less than the above-described range, extremely poor effects in preventing fading or discoloration of color images and discoloration of background are achieved and thus it is practically unsuitable. On the other hand, if the compound of the general formula (I) is used in an amount larger than the above-described range, it can inhibit process of development and cause reduction of color density.

In practicing the present invention, known antifading agents can be used together with the compound of the general formula (I), and the color image stabilizer of the present invention of the general formula (I) can be used individually or as a combination of two or more thereof. The amount of the known anti-fading agent is usually about 0.01 mol to about 10 mols per mol of the coupler but a particularly preferred amount is about 0.1 mol to about 2 mols per mole of the coupler. Known anti-fading agents which can be used include, for example, hydroquinone derivatives described in U.S. Pat. Nos. 2,360,290, 2,418,613, 2,675,314, 2,701,197, 2,704,713, 2,728,659, 2,732,300, 2,735,765, 2,710,801, 2,816,028, British Pat. No. 1,363,921, etc., gallic acid derivatives described in U.S. Pat. Nos. 3,457,079, 3,069,262, Japanese Patent Publication 13,496/68, etc., p-alkoxyphenols described in U.S. Pat. Nos. 2,735,765, 3,698,909, Japanese Patent Publication No. 20,977/74, etc., p-hydroxyphenol derivatives as described in U.S. Pat. Nos. 3,432,300, 3,573,050, 3,574,627, 3,764,337, etc.

To incorporate the compound of the present invention (color image stabilizer) into a photographic layer of a color light-sensitive material, it is possible, for example, to dissolve the compound in a low boiling organic solvent such as ethyl acetate, ethanol, etc., and directly add the solution thereof to a silver halide emulsion, to a coating for a photographic auxiliary layer or to a coupler emulsion mixture without emulsification. Further, it is suitable to dissolve the compound of the present invention (color image stabilizer) in a high boiling solvent such as dibutyl phthalate, tricresyl phosphate, etc., together with a coupler and, if desired, in the presence of a low boiling auxiliary solvent and add such to a silver halide emulsion or to a coating for a photographic auxiliary layer as an emulsion dispersion of the color image stabilizer alone or together with a coupler dispersed as oil droplets in a water-soluble protective colloid such as gelatin.

Illustrative photographic layers to which the compound of the present invention (color image stabilizer) can be added include coupler-containing silver halide light-sensitive emulsion layers (e.g., a red-sensitive silver halide emulsion layer, a green-sensitive silver halide emulsion layer, a blue-sensitive silver halide emulsion layer) and light-insensitive photographic auxiliary layers (e.g., a protective layer, a filter layer, an interlayer, a subbing layer, a color image receiving layer, etc.), in the color photographic light-sensitive material. In particular, it is preferred for the color image stabilizer of the present invention to be present in a magneta coupler-containing photographic layer. That is, the compound is particularly effective for preventing fading or discoloration of magenta images.

Typical examples of high boiling organic solvents which can be used for dispersing the color image stabilizer of the present invention alone or in combination with a coupler include butyl phthalate, dinonyl phthalate, butyl benzoate, diethylhexyl sebacate, butyl stearate, dinonyl maleate, tributyl citrate, tricresyl phosphate, dioctylbutyl phosphate, trihexyl phosphate, trioctadecyl phosphate, etc., as described in U.S. Pat. No. 3,676,137, diethyl succinate, dioctyl adipate, 3-ethylbiphenyl, liquid dye stabilizers described, as improved photographic dye image stabilizers, in *Product Licensing Index*, Vol. 83, pp. 26–29 (March, 1971).

Examples of low boiling organic solvents which can be used as auxiliary solvents together with a high boiling organic solvent include ethyl acetate, butyl acetate, ethyl propionate, ethyl formate, butyl formate, nitroethane, carbon tetrachloride, chloroform, hexane, cyclohexane, ethylene glycol, acetone, ethanol, dimethylformamide, dioxane, etc. In addition, it is also possible to use benzene, toluene, xylene, etc., with these solvents.

It is possible to dissolve the coupler used in this invention in the light boiling solvent described above, if desired, in the presence of the low boiling auxiliary solvent described above, and incorporate the coupler into a photographic layer of a color light-sensitive material as an emulsiondispersion.

Surface active agents can also be used in dispersing a solution of the color image stabilizer alone or in combination with a coupler in an aqueous protective colloid solution, and illustrative examples thereof include saponin, sodium alkylsulfosuccinates, sodium alkylbenzenesulfonates, etc., and examples of the hydrophilic protective colloid which can be used are gelatin, casein, carboxymethyl cellulose, polyvinyl alcohol, polyvinyl pyrrolidone, styrene-maleic anhydride copolymers, condensates of styrene-maleic anhydride copolymers and polyvinyl alcohol, polyacrylic acid salts, ethyl cellulose, etc. However, the present invention is not limited only to those examples.

The silver halide emulsion which can be used in this invention can be suitably selected from various kinds of photographic emulsions depending on the end-use purposes of the photographic materials. Suitable silver halides which can be used in this invention are silver chloride, silver chlorobromide, silver bromide, silver iodobromide, and silver chloroiodobromide. Also, suitable binders for the silver halide emulsions which can be used in this invention are the hydrophilic protective colloids described above, such as gelatin, gelatin derivatives, etc.

The silver halide emulsions used in this invention can be prepared by a single jet method, a double jet method, a control double jet method, and further the halogen conversion method as described in British Pat. No. 635,841 and U.S. Pat. No. 3,622,318.

The silver halide emulsion used in this invention can be sensitized by the natural sensitizers present in gelatin, by a sulfur sensitizer, by a reductive sensitizer, and by a noble metal salt using conventional techniques. Suitable examples of chemical sensitizers are auric compounds such as auric chloric compounds or auric trichloride compounds as disclosed in U.S. Pat. Nos. 2,399,083, 2,540,085, 2,597,856, 2,597,915, etc.; noble metal salts of platinum, palladium, iridium, rhodium, or ruthenium as disclosed in U.S. Pat. Nos. 2,448,060, 2,540,086, 2,566,245, 2,566,263, 2,598,079, etc.; sulfur compounds which react with silver salts to form silver sulfide as disclosed in U.S. Pat. Nos. 1,574,944, 2,410,689, 3,186,458, 3,501,313, etc.; reduction compounds of stannous salts or amine group compounds as disclosed in U.S. Pat. Nos. 2,487,850, 2,518,698, 2,521,925, 2,521,926, 2,694,637, 2,983,610, 3,201,254, etc.

The silver halide emulsion can further be stabilized using an agent for forming a sparingly soluble silver salt, such as a mercapto compound, e.g., 1-mercapto-5-phenyltetrazole and/or a stabilizer such as 5-methyl-6-oxy-1,3,4-triazaindolizine. For example, the photographic emulsion can contain compounds added to prevent a reduction in the sensitivity and fogging during the manufacturing process or on storage. Typical compounds are 4-hydroxy-6-methyl-1,3,3a,7-tetrazaindene, 3-methyl-benzothiazole, 1-phenyl-5-mercaptotetrazole, heterocyclic compounds, mercury containing compounds, mercapto compounds, and metal salts. Additional examples which can be used are disclosed in C.E.K. Mees and T. H. James, *The Theory of the Photographic Process*, 3rd Ed., Macmillan, New York (1966), and also in U.S. Pat. Nos. 1,758,576, 2,110,178, 2,131,038, 2,173,628, 2,697,040, 2,304,962, 2,324,123, 2,494,198, 2,444,605, 2,444,606, 2,444,607, 2,444,608, 2,566,245, 2,694,716, 2,697,099, 2,708,162, 2,178,633, 2,728,664, 2,728,665, 2,476,536, 2,824,001, 2,843,491, 2,886,437, 3,052,544, 3,137,577, 3,220,839, 3,226,231, 3,236,652, 3,251,691, 3,252,799, 3,287,135, 3,326,681, 3,420,668, 3,622,339, and British Pat. Nos. 893,428, 403,789, 1,173,609, 1,200,188. Furthermore, the photographic emulsion can contain a sensitizing dye such as a cyanine dye and merocyanine dye as described in U.S. Pat. Nos. 2,688,545, 2,912,329, 3,397,060, 3,615,635 and 3,628,964, British Pat. 1,195,302, 1,242,588 and 1,293,862, German Pat. Application (OLS) Nos. 2,030,326, and 2,121,780, Japanese Pat. Publication Nos. 4,936/68 and 14,030/69 and further a coating aid such as saponin, polyethylene glycol monolauryl ether, etc., for example, as described in U.S. Pat. Nos. 2,271,623, 2,240,472, 2,288,226, 2,739,891, 3,068,101, 3,158,484, 3,201,253, 3,210,191, 3,294,540, 3,415,649, 3,441,413, 3,442,654, 3,475,174, 3,545,974, etc. Furthermore, the silver halide emulsion can contain a thickener such as polystyrenesulfonic acid, etc., an ultraviolet absorber such as 2-(2-hydroxy-3,5-di-sec-butylphenyl)-5-methoxybenzotriazole, 4-methoxycyanocinnamic acid-n-dodecyl ester, etc., as disclosed in U.S. Pat. Nos. 2,685,512, 2,739,888, 2,719,086, 2,739,971, 2,747,996, 2,784,087, 3,253,921, 3,533,794, 3,004,896, 3,159,646 and 3,214,436, an antioxidant or a reducing agent such as sodium bisulfite, ascorbic acid, an aminophenol, a pyrogallol, gallic acid, a catechol, a resorcinol, and dihydroxynaphthalene, and an irradiation preventing dye such as an oxonol dye and a styryl dye.

According to one embodiment of this invention, the photographic color material comprises a support having thereon a blue-sensitive silver halide emulsion layer containing a yellow dye forming coupler, a green-sensitive silver halide emulsion layer containing a magenta dye forming coupler and a red-sensitive silver halide emulsion layer containing a cyan dye forming coupler.

The color photographic light-sensitive material of this invention can have, in addition to the above-described silver halide emulsion layers, auxiliary layers such as a protective layer, a filter layer, intermediate layers, an antihalation layer, and a backing layer.

The color photographic light-sensitive materials can include color photographic materials, comprising at least one photographic light-sensitive layer consisting of a multilayer unit, such as is described in U.S. Pat. No. 3,726,681, 3,516,831, 3,843,369, British Pat. Nos. 818,687 and 923,045, etc., and comprising a diffusion transfer color system, such as is described in U.S. Pat. No. 3,635,707, British Pat. Nos. 840,731, 1,038,331, 1,066,352, etc.

The hydrophilic polymer, particularly gelatin, forming the silver halide emulsion layers of the color photographic material of this invention can be hardened by various cross-linking agents, e.g., an inorganic compound such as a chromium salt and a zirconium salt, and an aldehyde type cross-linking agent as described in Japanese Pat. No. 1,872/1971. Examples of hardening agents which can be employed for this purpose are aldehyde compounds such as formaldehyde, glutaraldehyde, etc.; ketone compounds such as diacetyl, cyclopentanedione, etc.; reactive halogen containing compounds such as bis(2-chloroethylurea) and 2-hydroxy-4,6-dichloro-1,3,5-triazine, as disclosed in U.S. Pat. Nos. 3,288,775 and 2,732,303, British Pat. Nos. 974,723 and 1,167,207; compounds having a reactive olefinic group such as divinylsulfone, 5-acetyl-1,3-diacryloylhexahydro-1,3,5-triazine, etc., as described in the specifications of U.S. Pat. Nos. 3,635,718 and 3,232,763 and British Pat. No. 994,869; the N-methylol compounds such as N-hydroxymethylphthalimide, etc., as described in the specifications of U.S. Pat. Nos. 2,732,316 and 2,586,168; the isocyanates as described in the specification of U.S. Pat. No. 3,103,437; the organic carboxylic acid or sulfonic acid derivatives as described in the specifications of U.S. Pat. Nos. 2,725,294 and 2,725,295; the carbodiimide compounds as described in the specification of U.S. Pat. No. 3,100,704; the epoxy compounds as described in the specification of U.S. Pat. No. 3,091,537; the isooxazole compounds as described in the specifications of U.S. Pat. Nos. 3,321,313 and 3,543,292; halocarboxyaldehydes such as mucochloric acid; dioxane derivatives such as dihydroxydioxane, dichlorodioxane, etc.; and inorganic hardening agents such as chromium alum, zirconium sulfate, etc.

Also, precursors such as, for instance, an alkali metal bisulfite-aldehyde addition product, a methylol derivative of hydantoin, and a primary aliphatic nitro alcohol can be used instead of the above-described compounds as the hardening agent.

However, particularly useful cross-linking agents which can be used in this invention are the polyepoxy compounds as described in Japanese Pat. No. 7,133/1959, the poly-(1-aziridinyl) compounds as described in Japanese Pat. No. 8,790/1962, and the active halogen compounds as described in U.S. Pat. Nos. 3,362,827 and 3,325,287.

Suitable supports which can be used in the present invention include those which are commonly used for photographic light-sensitive materials such as a cellulose nitrate film, a cellulose acetate film, a cellulose acetate butyrate film, a cellulose acetate propionate film, a polystyrene film, a polyethylene terephthalate film, a polycarbonate film, a laminate of these films, a thin glass plate, paper, and the like. Papers coated or laminated with baryta or an α-olefin polymer, in particular, a polymer of an α-olefin having 2 to 10 carbon atoms such as polyethylene, polypropylene, an ethylene-butene copolymer, etc., synthetic resin films whose surface has been roughened to improve intimately the adhesive property with other polymers as described in Japanese Pat. Publication No. 19,068/72 also provide good results.

Suitable supports include transparent or opaque supports which are selected depending upon the end-use of the light-sensitive materials. Also, transparent supports colored with a dye or pigment can be used as well.

Suitable opaque supports include intrinsically opaque supports like paper and, in addition, that prepared by adding dyes or pigments like titanium oxide to a transparent film, a synthetic resin film which has been surface-treated according to the method described in Japanese Pat. Publication No. 19,068/72, papers or synthetic resin films to which carbon black, a dye or the like has been added to render them completely light-intercepting, and the like. A subbing layer is usually provided on the support. The surface of the support may be subjected to a preliminary processing such as a corona discharge, an irradiation with ultraviolet light, a flame treatment, etc.

In practicing the present invention, it is naturally additionally effective and advantageous to prevent fading or discoloration by light to provide an ultraviolet light-absorbing layer on the upper surface of a photographic light-sensitive image-forming layer upon coating on a support.

The present invention is not limited by the kinds of conventionally used color processing agents such as color developing agents, bleaching agents, fixing agents, etc. In particular, the present invention can advantageously be employed in silver-saving type color light-sensitive materials described in U.S. Pat. Nos. 3,902,905, 3,674,490, 3,765,891, etc. Also, the present invention is not limited by the kind of intensifying agents to be used for color intensifying processing as described in German Pat. Application (OLS) No.

181,390, Japanese Pat. Application (OPI) No. 9,728/73, Japanese Pat. Application No. 128,327/74, etc.

The present invention is applicable to ordinary color light-sensitive materials, e.g., a color negative film, a color positive film, a color reversal film, a color printing paper, etc., in particular, color light-sensitive materials for color prints. Further, it is applicable to the color photographic system described in U.S. Pat. Nos. 3,227,550, 3,227,551, 3,227,552, U.S. Provisional Patent Publication No. U.S.B. 351,673, etc., in particular, to the color diffusion transfer photographic system.

Color photograhic development processing is necessary after exposure in order to obtain dye images using the color photographic light-sensitive material of the present invention. Color photographic development processing fundamentally involves a color developing step, a bleaching step, and a fixing step. In some cases, two of these steps are conducted in one processing. In addition, a combination of color development, first fixing and bleach-fixing is also possible. The development processing step is combined with, if necessary, a prehardening bath, a neutralizing bath, a first development (black-and-white development), an image-stabilizing bath, a washing or the like. A suitable processing temperature is in many cases about 18° C or above. Particularly, the processing temperature can be about 20° C to 60° C, and more recently about 30° C to about 60° C.

A suitable color developer which can be used is an alkaline aqueous solution having a pH of about 8 or higher, preferably 9 to 12, containing a color developing agent. Preferred typical examples of the above-described color developing agent are 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 4-amino-3-methyl-N-ethyl-N-β-methanesulfoamidoethylaniline, 4-amino-N,N-dimethylaniline, 4-amino-3-methoxy-N,N-diethylaniline, 4-amino-3-methyl-N-ethyl-N-β-methoxyethylaniline, 4-amino-3-methoxy-N-ethyl-N-β-methoxyethylaniline, 4-amino-3-β-methanesulfoamido-ethyl-N,N-diethylaniline, and the salts thereof (e.g., sulfates, hydrochlorides, sulfites, p-toluenesulfonates, etc.). Other examples are described in U.S. Pat. Nos. 2,193,015, 2,592,364, Japanese Patent Application (OPI) 64,933/73, L.F.A. Mason, *Photographic Processing Chemistry*, pp. 226 - 229, Focal Press, London (1966), etc.

The color developer can further contain pH buffers such as alkali metal sulfites, carbonates, borates or phosphates, development inhibitors or anti-fogging agents such as bromides, iodides or organic anti-fogging agents.

Specific examples of the anti-fogging agents include potassium bromide, potassium iodide, nitrobenzimidazoles described in U.S. Pat. Nos. 2,496,940 and 2,656,271, mercaptobenzimidazole, 5-methylbenzotriazole, 1-phenyl-5-mercaptotetrazole, compounds described in U.S. Pat. Nos. 3,113,864, 3,342,596, 3,295,976, 3,615,522, 3,597,199, etc., thiosulfonyl compounds described in British Pat. No. 972,211, phenazine-N-oxides as described in Japanese Patent Publication 41/675/71, anti-fogging agents described in *Kagaku Shashin Binran*, Vol. II, pp. 29 - 47, and the like.

In addition, the color developer may contain, if desired, a water softener, a preservative such as hydroxylamine, an organic solvent such as benzyl alcohol, diethylene glycol, etc., a development accelerator such as polyethylene glycol, a quaternary ammonium salt, an amine, etc., a dye-forming coupler, a competitive coupler, a fogging agent such as sodium borohydride, an auxiliary developing agent such as 1-phenyl-3-pyrazolidone, a viscosity-imparting agent, and the like.

The color light-sensitive material of the present invention can be subjected to ordinary color development processing or to the following color intensifying development processing: for example, a processing using peroxides described in U.S. Pat. Nos. 3,674,490, 3,761,265, German Pat. Application (OLS) No. 2,056,360, Japanese Pat. Application (OPI) No. 10,538/72, Japanese Patent Application Nos. 89,898/75, 89,897/75, 89,899/75, etc.; a processing using cobalt complex salts described in German Pat. Application (OLS) No. 2,266,770, Japanese Pat. Applications (OPI) Nos. 9,728/73, 9,729/73, Japanese Pat. Applications Nos. 76,101/74, 20,196/75, 57,041/75, 83,863/75, 87,484/75, etc.; and a processing using chlorous acid described in Japanese Pat. Application Nos. 128,327/74, 139,917/74, 27,784/75, etc.

After color development processing, the photographic emulsion layer is usually subjected to bleaching. Bleaching may be conducted either simultaneously with fixing or independently thereof. Suitable bleaching agents which can be used include compounds of multivalent metals such as iron(III), cobalt(III), chromium(VI), copper(II), etc., peracids, quinones, nitroso compounds, etc. For example, ferricyanides, dichromates, organic complex salts of iron(III) or cobalt(III), complex salts of aminopolycarboxylic acids (e.g., ethylene-diaminetetraacetic acid, nitrilotriacetic acid, 1,3-diamino-2-propanoltetraacetic acid, etc.) or of organic acids (e.g., citric acid, tartaric acid, malic acid, etc.); persulfates, permanganates; nitrosophenol, etc., can be used. Of these, potassium ferricyanide, iron(III) sodium ethylendiaminetetraacetate and iron(III) ammonium ethylenediaminetetraacetate are particularly useful. Ethylenediaminetetraacetic acid-iron(III) complex salt is effective in a bleaching solution and in a monobath bleach-fixing solution.

Various additives including bleaching-accelerators described in U.S. Pat. Nos. 3,042,520, 3,241,966, Japanese Pat. Publication Nos. 8,506/70, 8,836/70, etc., can be added to the bleaching solution or bleach-fixing solution.

The present invention is illustrated in greater detail by reference to the following examples which, however, are not to be construed as limiting the present invention in any way.

EXAMPLE 1

10 g of 1-(2,4,6-trichlorophenyl)-3-(2-chloro-5-tetradecanamido)anilino-5-pyrazolone (as a magenta coupler) and 2 g of Compound (1) used in this invention (as an image stabilizer) were dissolved in a mixture of 5 ml of tricresyl phosphate and 10 ml of ethyl acetate, and the resulting solution was emulsified and dispersed in 80 g of a 10% gelatin aqueous solution containing sodium dodecylbenzenesulfonate. Then, this emulsion dispersion was mixed with 145 g of a green-sensitive silver chlorobromide emulsion (Br: 70 mol%) (containing 7 g of silver) and, after adding thereto a hardener and a coating aid, it was coated on a paper support, in an amount of 400 mg/m$^2$ in terms of the coupler, both sides of which were laminated with polyethylene, then dried (Sample I).

In the same manner, the following samples were prepared.

| Sample | Color Image Stabilizer | Amount Added/10 g Coupler | |
|---|---|---|---|
| I | Compound (1) | 2 g | Present Invention |
| II | None | — | Comparative Sample |
| III | 2,5-Di-tert-butyl-hydroquinone | 2 g | " |
| IV | D,L-α-Tocopherol | 2 g | " |
| V | Comparative Compound* | 2 g | " |

*Comparative Compound

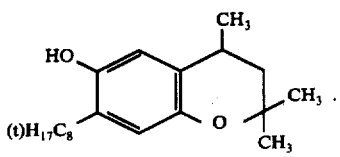

After exposing these samples for 1 second to light of 1,000 lux, they were processed with the following processing solutions.

| Developer Solution | |
|---|---|
| Benzyl Alcohol | 15 ml |
| Na₂SO₃ | 5 g |
| KBr | 0.4 g |
| Hydroxylamine Sulfate | 2.0 g |
| 4-Amino-3-methyl-N-ethyl-N-β-(methane-sulfonamido)ethylaniline | 10.0 g |
| Na₂CO₃ | 30.0 g |
| Diethylenetriaminepentaacetic Acid | 5.0 g |
| Water to make | 1,000 ml |
| | (pH 10.1) |
| Bleach-Fixing Solution | |
| Ammonium Thiosulfate (70% aq. soln.) | 150 ml |
| Na₂SO₃ | 15 g |
| Na[Fe(EDTA)] | 40 g |
| EDTA | 4 g |
| Water to make | 1,000 ml |
| | (pH 6.8) |

| Processing Step | Temperature (° C) | Time |
|---|---|---|
| Developer | 33 | 3 min 30 sec |
| Bleach-Fixing Solution | 33 | 1 min 30 sec |
| Washing | 28 – 35 | 3 min |
| Drying | | |

Each of the thus obtained samples containing dye images was subjected to a fading test for 4 weeks using a fluorescent lamp fading tester (20,000 lux) equipped with an ultraviolet light-absorbing filter, C-40, absorbing light of a wavelength of 400 nm or shorter (made by Fuji Photo Film Co., Ltd.).

The results obtained are shown in Table 1 below. The fading degree is indicated in terms of the change in density of the area whose density before the fading testing was 2.0 and of fogged areas (background), caused by the fading testing.

The fogged areas showed the change in yellow density.

TABLE 1

| | Density Change Caused by Fading Testing | | |
|---|---|---|---|
| Sample | Fogged Areas | Areas of 2.0 in Density | Comments |
| I | +0.10 | −0.20 | Present Invention |
| II | +0.30 | −0.80 | For Comparison |
| III | +0.25 | −0.55 | " |
| IV | +0.30 | −0.60 | " |

TABLE 1-continued

| | Density Change Caused by Fading Testing | | |
|---|---|---|---|
| Sample | Fogged Areas | Areas of 2.0 in Density | Comments |
| V | +0.25 | −0.30 | " |

The results in this table show that the color images of the sample of the present invention have greatly improved stability to light and are superior to those of Samples III, IV and V obtained using known color image stabilizers. In particular, the color image stabilizer used in Sample V depresses yellow degree of fogged areas to a lesser extent, although it is excellent in the other property. Thus, it can be seen that the compound used in the present invention is quite excellent in stabilizing color images and in preventing discoloration of backgrounds.

EXAMPLE 2

In the same manner as described in Example 1, an emulsion dispersion for a green-sensitive layer was prepared and samples having the following layer structure was prepared.

| Layer | |
|---|---|
| Sixth Layer: | Gelatin 1,000 mg/m² |
| Fifth Layer: | Red-sensitive layer (RL), Silver halide emulsion AgBrCl (Br: 50 mol%), Silver 200 mg/m², Cyan coupler*1 400 mg/m², Gelatin 1,000 mg/m², Coupler solvent*2 200 mg/m² |
| Fourth Layer: | Gelatin 1,200 mg/m², Ultraviolet light-absorbing agent*8 1,000 mg/m² |
| Third Layer: | Green-sensitive layer (GL), Silver halide emulsion AgBrCl (Br: 50 mol%), Silver 400 mg/m², Magenta coupler*3 300 mg/m², Color image stablizer*7, Coupler solvent*4 300 mg/m² |
| Second Layer: | Gelatin 1,000 mg/m² |
| First Layer: | Blue-sensitive layer (BL), Silver halide emulsion AgBrCl (Br: 80 mol%), Silver 400 mg/m², Gelatin 1,200 mg/m², Yellow coupler*5 300 mg/m², Coupler solvent*2 150 mg/m² |
| Support*6 | |

*1Coupler: 2-[α-(2,4-Di-t-amylphenoxy)butyramido]-4,6-dichloro-5-methylphenol
*2Solvent: Dibutyl phthalate
*3Coupler: 1-(2,4,6-Trichlorophenyl)-3-[2-chloro-5-tetradecanamido]anilino-5-pyrazolone
*4Coupler solvent: Tricresyl phosphate
*5Coupler: α-Pivaloyl-α-[2,4-dioxo-5,5'-dimethyloxazolidin-3-yl]-2-chloro-5-[α-(2,4-di-t-amylphenoxy)butanamido]acetanilide
*6Paper support both sides of which were laminated with polyethylene containing titanium dioxide dispersed therein
*7See Table 2 below
*82-(2-Hydroxy-3-sec-butyl-5-tert-butylphenyl)benzotriazole

TABLE 2

| Sample | Color Image Stabilizer | Amount Added Based on Coupler (wt%) | Comments |
|---|---|---|---|
| VI | None | | For Comparison |
| VII | 2,5-Di-tert-octyl-hydroquinone | 30 | " |
| VIII | Compound 7 | 30 | Present Invention |
| IX | Compound 7 2,5-Di-t-octyl-hydroquinone | 30 20 | " |

These samples were subjected to the same processing as described in Example 1 and to the fading testing for 4 weeks using the fluorescent lamp fading tester as described in Example 1. The results obtained are shown in Table 3 below.

TABLE 3

| Sample | Change of Yellow Density in Fogged Area | Change of Density in Area Where Magenta Density Was Maximum |
|---|---|---|
| VI | +0.30 | −0.80 |
| VII | +0.28 | −0.70 |
| VIII | +0.20 | −0.40 |
| IX | +0.10 | −0.25 |

The samples of the present invention were greatly improved in the stability of color images, and the combined use with a known color image stabilizer (2,5-di-tert-octylhydroquinone) further improved the property of depressing the change in the yellow density of the fogged areas and improved the color image stability.

While the invention has been described in detail and with reference to specific embodiments thereof, it will be apparent to one skilled in the art that various changes and modifications can be made therein without departing from the spirit and scope thereof.

What is claimed is:

1. A color photographic silver halide lightsensitive material containig a coupler therein and, in at least one photographic layer, a compound represented by the following general formula (I):

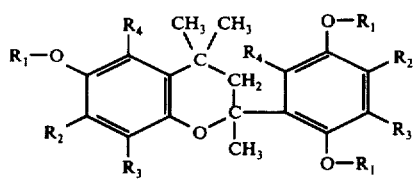

wherein $R_1$ represents a hydrogen atom or an —X—Y group wherein X represents a carbonyl group or a sulfonyl group, and Y represents a straight chain, brànched chain or cyclic alkyl group having 1 to 20 carbon atoms, an aryl group, an aralkyl group, an alkoxy group containing a straight chain, branched chain or cyclic alkyl group having 1 to 20 carbon atoms, an aryloxy group, an aralkoxy group, a straight chain, branched chain or cyclic alkoxycarbonyl group having 2 to 20 carbon atoms, an aryloxycarbonyl group, or an aralkoxycarbonyl group; and $R_2$, $R_3$ and $R_4$, which may be the same or different, each represents a hydrogen atom, a straight chain, branched chain or cyclic alkyl group having 1 to 20 carbon atoms, a straight chain, branched chain or cyclic alkoxy group having 1 to 20 carbon atoms, an aryl group, an aryloxy group, an aralkyl group, an aralkoxy group, an alkenyl group, an alkenoxy group, an acylamino group, a halogen atom, an alkylthio group containing a straight chain, branched chain or cyclic alkyl group having 1 to 20 carbon atoms, an aryl group, a diacylamino group, an acyl group having 1 to 20 carbon atoms, a sulfonamido group, a straight chain, branched chain or cyclic alkylamino group having 1 to 20 carbon atoms, a straight chain, branched chain or cyclic alkoxycarbonyl group having 2 to 20 carbon atom or an acyloxy group having 1 to 20 carbon atoms, provided that $R_2$, $R_3$ and $R_4$ do not simultaneously represent hydrogen atoms, wherein said coupler is a magenta coupler represented by the general formula (II) or (III);

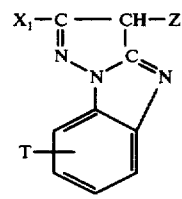

wherein W represents a hydrogen atom or has up to 35 carbon atoms and represents a straight chain or branched chain alkyl group, an alkenyl group, a cycloalkyl group, an aralkyl group, or a cycloalkenyl group, which groups may be substituted with one or more substituents selected from the group consisting of a hydrogen atom, a nitro group, a cyano group, a monoaryl group, an alkoxy group, a monoaryloxy group, a carboxy group, an alkylcarbonyl group, a monoarylcarbonyl group, an alkoxycarbonyl group, a monoaryloxycarbonyl group, a sulfo group, an acyloxy group, a sulfamoyl group, a carbamoyl group, an acylamino group, a imido group, a ureido group, a thioureido group, a urethane group, a thiourethane group, a sulfonamido group, a heterocyclic group, an arylsulfonyloxy group, an alkylsulfonyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-arylanilino group, an N-alkylanilino group, an N-acylanilino group, a hydroxy group and mercapto group; an aryl group and an aryl group having 1 to 5 substituents selected from the group consisting of a halogen atom, an alkyl group, an alkenyl group, a monocycloalkyl group, an aralkyl group, a monocycloalkenyl group, a nitro group, a cyano group, a mono- or polycyclic aryl group, an alkoxy group, a mono- or polycyclic aryloxy group, a carboxy group, an alkylcarbonyl group, an arylcarbonyl group, an alkoxycarbonyl group, an aryloxycarbonyl group, a sulfo group, an acyloxy group, a sulfamoyl group, a carbamoyl group, an acylamino group, an imido group, a ureido group, a thioureido group, a urethane group, a thiourethane group, a sulfonamido group, a heterocyclic group, an arylsulfonyloxy group, an alkylsulponyloxy group, an arylsulfonyl group, an alkylsulfonyl group, an arylthio group, an alkylthio group, an alkylsulfinyl group, an arylsulfinyl group, an alkylamino group, a dialkylamino group, an anilino group, an N-alkylanilino group, an N-arylanilino group, an N-acylanilino group, a hydroxy group and a mercapto group; a heterocyclic group or a heterocyclic group substituted with one or more substituents above described for the aryl group for W; an acyl group a thioacyl group; an alkylsulfonyl arylsulfonyl group; an alkylsulfinyl group; an arylsulfinyl group; a carbamoyl group; or a thiocarbamoyl group;

$X_1$ represents a hydrogen atom or has up to 35 carbon atoms and represents a straight chain or branched chain alkyl group, an alkenyl group, a cycloalkyl group, an aralkyl group and a cycloalkenyl group, which groups may be substituted with one or more substituents as described above for these groups for W; an aryl group or a heterocyclic group, each of which can be substituted with one or more substituents as described above the aryl group and the heterocyclic group for W; an alkoxycarbonyl group; an aryloxycarbonyl group; an aralkyloxycarbonyl group; an alkoxy group; an aryloxy group; an arylthio group; a carboxy group; an acylamino group; an imido group; an N-alkylacylamino group; an N-arylacylamino group; a ureido group; a thioureido group; a urethane group; a thiourethane group; an anilino group; an alkylamino group; a cycloamino group; an alkylcarbonyl group; an arylcarbonyl group; a sulfonamido group; a carbamoyl group; a sulfamoyl group; a guanidino group; a cyano group; an acyloxy group; a sulfonyloxy group; a hydroxy group; a mercapto group; a halogen atom; or sulfo group;

T represents a hydrogen atom or has up to 35 carbon atoms and represents a straight chain or branched chain alkyl group, an alkenyl group, a cycloalkyl group, an aralkyl group, and a cycloalkenyl group which may be substituted with one or more substituents as described above for these groups for W; an aryl group or a heterocyclic group, each of which may be substituted with one or more substituents as described above for the aryl group and the heterocyclic group for W; a halogen atom; a cyano group; an alkoxy group; an aryloxy group; a carboxy group; an alkoxycarbonyl group; an aryloxycarbonyl group; an acyloxy group; an alkylcarbonyl group; an arylcarbonyl group; an alkylthiocarbonyl group; a sulfo group; a salfamoyl group; a carbamoyl group; an arylthiocarbonyl group; an acylamino group; an imido group; a ureido group; a thioureido group; a urethane group; a thiourethane group; a sulfonamido group; an alkylsulfonyloxy group; an arylsulfonyloxy group; an arylsulfonyl group; an alkylsulfonyl group; an arylthio group; an alkylthio group; an alkylsulfinyl group; an arylsulfinyl group; an alkylamino group; a dialkylamino group; an anilino group; an N-arylanilino group; an N-alkylanilino group; an N-acylanilino group; a hydroxy group; or a mercapto group; and Z represents a hydrogen atom or a coupling-off group bonded to the coupling position through an oxygen atom, a nitrogen atom or a sulfur atom.

2. The color photographic light-sensitive material according to claim 1, wherein $R_1$ represents a hydrogen atom or an —X—Y group wherein Y represents a methyl group, an ethyl group, a t-butyl group, a cyclohexyl group, a dodecyl group, an octadecyl group, a heptadecyl group, a β-acetylaminopropyl group, a phenyl group, p-tolyl group, a p-methoxyphenyl group, an m-nitrophenyl group, an o-chlorophenyl group, an α-naphthyl group, a β-naphthyl group, a benzyl group, a phenethyl group, a methoxy group, a t-butoxy group, a cyclohexyloxy group, a dodecyloxy group, an octadecyloxy group, a phenoxy group, a p-tolyloxy group, a p-metoxyphenyloxy group, an isopropylphenoxy group, an m-nitrophenoxy group, an o-chlorophenoxy group, an α-naphthyloxy group, a β-naphthyloxy group, a benzyloxy group, a phenethyloxy group, a methoxycarbonyl group, a t-butoxycarbonyl group, a cyclohexyloxycarbonyl group, an octyloxycarbonyl group, an ethoxycarbonyl group, a phenoxycarbonyl group, a p-tolyloxycarbonyl group, a p-methoxyphenyloxycarbonyl group, an m-nitrophenoxycarbonyl group, an o-chlorophenoxycarbonyl group, a benzyloxycarbonyl group, a phenethyloxycarbonyl group; $R_2$, $R_3$ and $R_4$ each represents a hydrogen atom, a methyl group, a t-butyl group a cyclopentyl group, a cyclohexyl group, a t-octyl group, a dodecyl group, an octadecyl group, a β-acetamidopropyl group, a methoxy group, a t-butoxy group, a cyclohexyl group, a dodecyloxy group, an octadecyloxy group, a phenyl group, a p-tolyl group, a p-methoxyphenyl group, a p-octadecanoylaminophenyl group, an o-chlorophenyl group, an o-tolyl group, an m-nitrophenyl group, an α-naphthyl group, a phenoxy group, an α-naphthoxy group, a p-tolyloxy group, a p-methoxyphenyloxy group, a p-hexanoylaminophenoxy group, an o-chlorophenoxy group, an m-nitrophenoxy group, a benzyl group, a phenethyl group, a benzyloxy group, a phenethyloxy group, an allyl group, an allyloxy group, an acetylamino group, a benzoylamino group, a caproylamino group, a chlorine atom, a methylthio group, a t-butylthio group, a hexylthio group, a cyclohexylthio group, a dodecylthio group, a phenylthio group, a p-tolylthio group, an o-carboxyphenylthio group, an o-tolylthio group, an m-methoxycarbonylphenylthio group, an m-nitrophenyl group, a succinimido group, a 3-hydantoinyl group, an acetyl group, a caproyl group, a p-methoxybenzoyl group, an ethylamino group, a t-butylamino group, a dioctylamino group, an octadecylamino group, a methoxycarbonyl group, a t-butoxycarbonyl group, an octadecylcarbonyl group, an acetoxy group, a caproyloxy group, a lauroyloxy group or a benzoyloxy group.

3. The color photographic light-sensitive material according to claim 2, wherein said compound represented by the general formula (I) is selected from the group consisting of compounds of the formula:

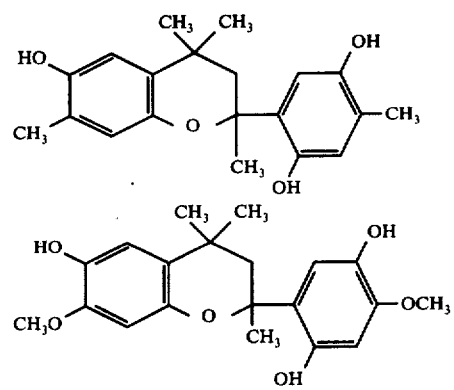

-continued
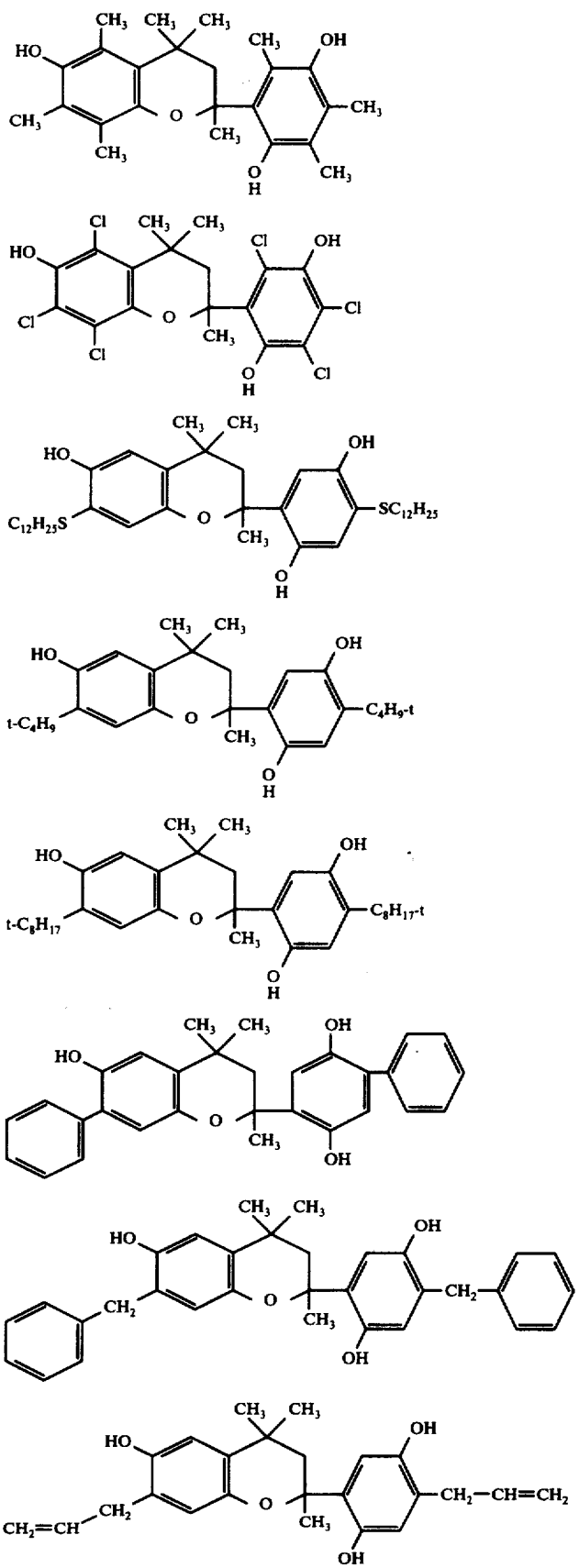

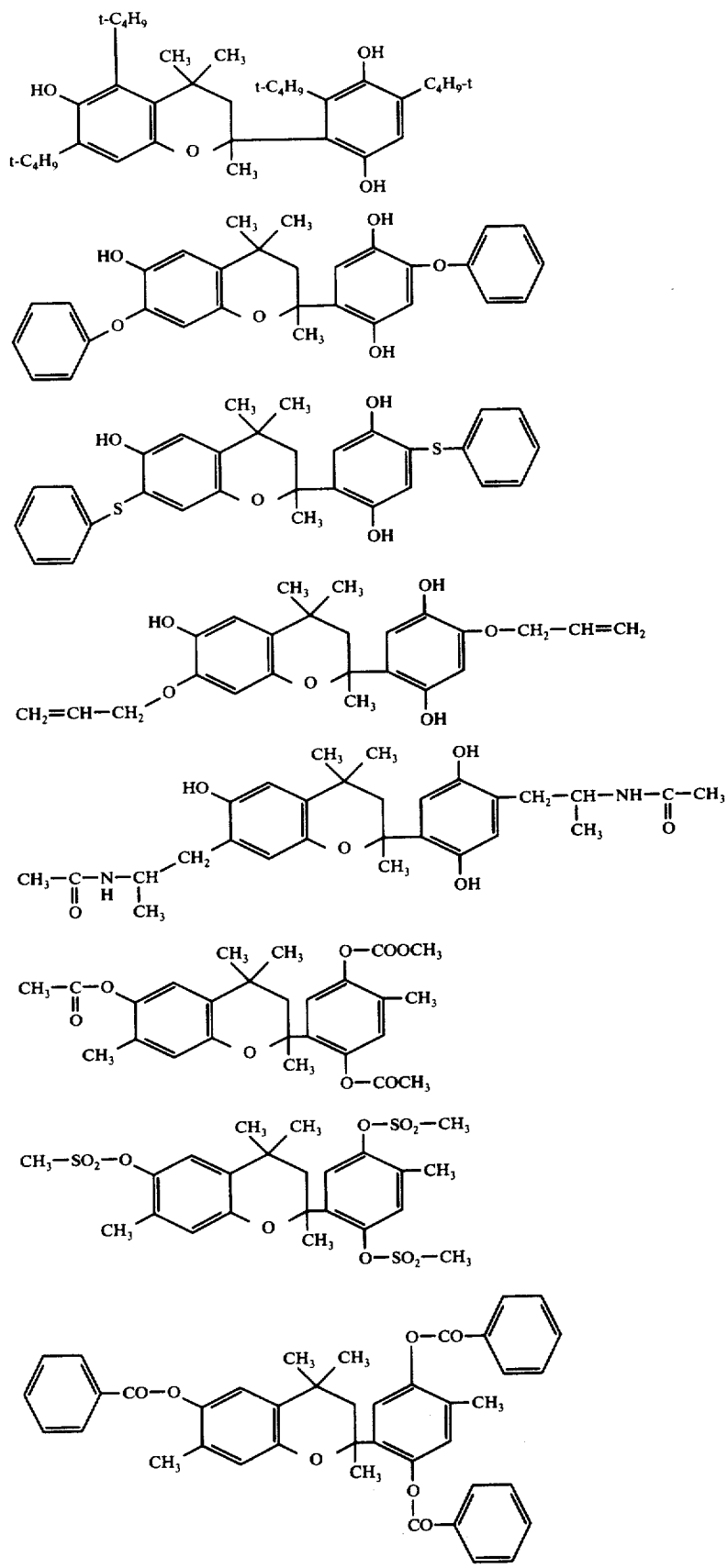

-continued
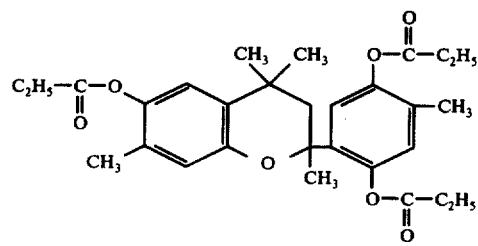
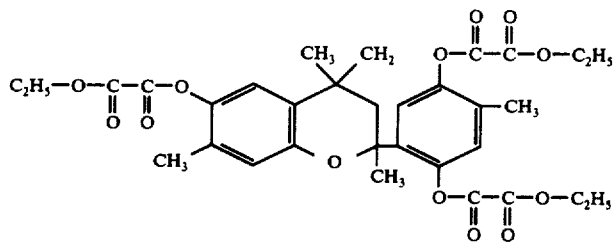
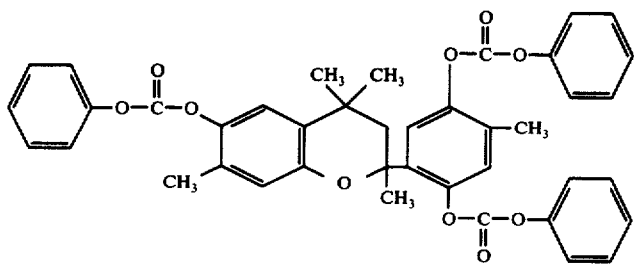
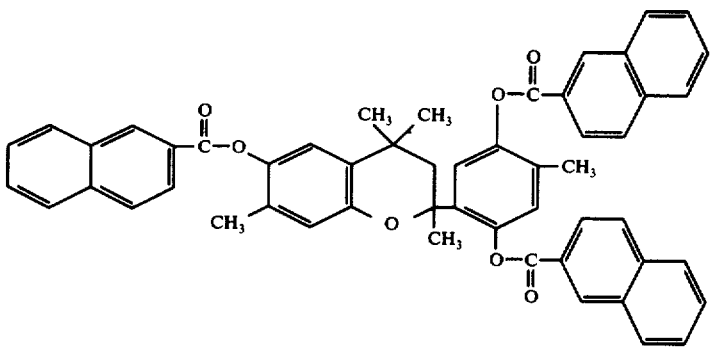
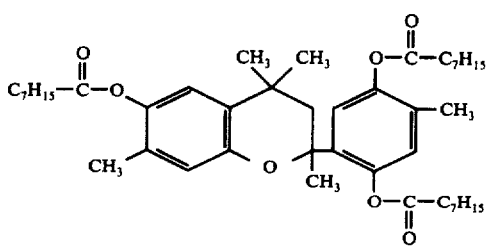
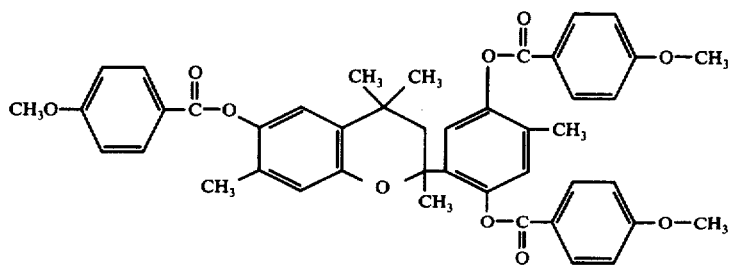
and

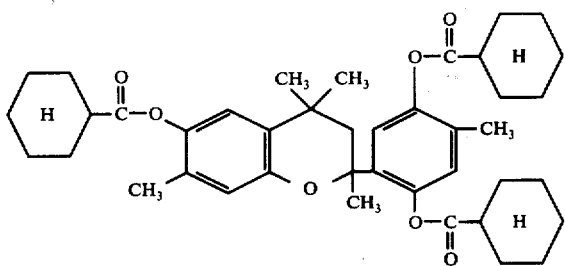

4. The color photographic light-sensitive material according to claim 1, wherein said magenta coupler is a coupler selected from the group consisting of:

1-(2,4,6-trichlorophenyl)-3-{3-[α-(2,4-di-tert-amylphenoxy)butyramido]benzamido}-5-oxo-2-pyrazoline 1-(2,4,6-trichlorophenyl)-3-[3-(α-ethoxycarbonyloctadecanamido)benzamido]-5-oxo-2-pyrazoline 1-(2,4-dimethyl-6-chlorophenyl)-3-{3-[(2,4-di-tert-amylphenoxy)acetamido]benzamido}-5-oxo-2-pyrazoline 1-(2,4,6-trichlorophenyl)-3-{3-[(2,4-di-tert-amylphenoxy)acetamido]benzamido}-5-oxo-2-pyrazoline-4-ylbenzylcarbonate 1-[4-(4-tert-amylphenoxy)phenyl]-3-[α-(4-tert-amylphenoxy)propionamido]-5-oxo-2-pyrazoline 1-(2,4,6-trichlorophenyl)-3-(2-chloro-5-tetradecanamido)anilino-5-oxo-2-pyrazoline 1-(2,6-dichloro-4-methoxyphenyl)-3-{2-chloro-5-[α-(2,4-di-tert-amylphenoxy)butyramido]anilino}-4-phenylthio-5-oxo-2-pyrazoline 1-(2,6-dichloro-4-methoxyphenyl)-3-{3-[α-(3-n-pentadecylphenoxy)butyramido]benzamido}-5-oxo-2-pyrazoline 1-(2,4-dimethyl-6-chlorophenyl)-3-{3-[β-dodecyloxycarbonyl)propionamido]benzamido}-5-oxo-2-pyrazoline 1-(2,4,6-trichlorophenyl)-3-{2-chloro-5-[α-(4-methoxyphenoxy)tetradecanamido]anilino}-5-oxo-2-pyrazoline 1-(2,4,6-trichlorophenyl)-3-{3-[α-(2,4-di-tert-amylphenoxy)butyramido]benzamido-4-imidazolyl}-5-oxo-2-pyrazoline 1-(2,4,6-trichlorophenyl)-3-{2-chloro-5-[α-(3,5-di-tert-butyl-4-hydroxyphenoxy)tetradecanamido]anilino}-5-oxo-2-pyrazoline 1-(2,6-dichloro-4-methylphenyl)-3-{3-[(3-n-pentadecylphenoxy)acetamido]benzamido}-5-oxo-2-pyrazoline 1-(2,4,6-trichlorophenyl)-3-{γ-[2-hydroxy-3-(2-benzotriazolyl)-5-n-pentylphenyl]butyramido}-5-oxo-2-pyrazoline 1-(2,4,6-trichlorophenyl)-3-{2-chloro-5-[β-dodecyloxycarbonyl)ethylcarbonyl]anilino}-5-oxo-2-pyrazoline 1-(2,4,6-trichlorophenyl)-3-[3-(dodecylureido)benzamido]-5-oxo-2-pyrazoline 1-(2,4,6-trichlorophenyl)-3-[α-(2,4-di-tert-amylphenoxy)butyramido]-4-pentafluorobenzamido-5-oxo-2-pyrazoline 1-(2,6-dichloro-4-tetradecyloxycarbonylphenyl)-3-(2-chloro-5-methoxycarbonylanilino)-5-oxo-2-pyrazoline 1-(2,4,6-trichlorophenyl)-3-(α-carboxymethyl-n-2-eicosenamido)benzamido-5-oxo-2-pyrazoline 1-{4-[(2,4-di-tert-amylphenoxy)acetamido]phenyl}-3-(3-acetamido-benzamido)-5-oxo-2-pyrazoline 1-(2,4,6-trichlorophenyl)-3-{3-[(2-tetradecyl-4-chlorophenoxy)acetamido]benzamido}-5-oxo-2-pyrazoline 1-(2,4-dimethyl-6-chlorophenyl)-3-{3-[α-(2,4-di-tert-amylphenoxy)butyramido]phenylureido}-5-oxo-2-pyrazoline 1-(2,4,6-trichlorophenyl)-3-{3-[α-(2,4-di-tert-amylphenoxy)butyramido]benzamido}-4-phenylsulfonamido-5-oxo-2-pyrazoline 1-(2,4,6-trichlorophenyl)-3-{2-chloro-5-[α-(3-tert-butyl-4-hydroxyphenoxy)tetradecanamido]anilino}-5-oxo-2-pyrazoline 1-(2,4,6-trichlorophenyl)-3-{2-chloro-5-[β-(2,2-dimethyl-6-hydroxy-7-tert-octyl-4-chromanyl)propionamido]-anilino}-5-oxo-2-pyrazoline 2-{3-[α-(2,4-di-tert-amylphenoxy)butyramido]-benzamido}-7-chloropyrazolo-[1,5a]-benzimidazole 1-(2,4,6-trichlorophenyl)-3-{[2-chloro-5-(3,5-di-carboxyphenoxy-acetamido)]anilino}-4-[(4-N-methyl-N-octadecyl-sulfamoyl)phenoxy]-5-oxo-2-pyrazoline 1-(2-methylphenyl)-3-(3,5-dicarboxyanilino)-4-(3-octadecylcarbamoylphenylthio)-5-oxo-2-pyrazoline 1-(2,6-dichloro-4-methoxycarbonylphenyl)-3-{3-[α-(3-pentadecylphenoxy)butyramido]benzamido}-5-oxo-2-pyrazoline 1-(2,4,6-trichlorophenyl)-3-{3-[(2,4-di-tert-amylphenoxy)acetamido]benzamido}-4-(4-methoxyphenylazo)-5-oxo-2-pyrazoline 1-(2,4,6-trichlorophenyl)-3-(2-chloro-5-tetradecanamidoanilino)-4-(3-methyl-4-hydroxyphenylazo)-5-oxo-2-pyrazoline, and 1-(2,4,6-trichlorphenyl)-3-{2-chloro-5-[3-(2-dodecylcarbamoylethylthio)propanamido]anilino}-5-oxo-2-pyrazoline.

5. The color photographic light-sensitive material according to claim 1, wherein said compound represented by the general formula (I) is present in an amount of about 0.5 to about 200% by weight based on the weight of the coupler.

6. The color photographic light-sensitive material according to claim 1, wherein said compound represented by the general formula (I) is present in an amount of 2 to 150% by weight based on the weight of the coupler.

7. The color photographic light-sensitive material according to claim 1, wherein said at least one photographic layer is a silver halide light-sensitive emulsion layer.

8. The color photographic light-sensitive material according to claim 7, wherein said silver halide light-sensitive emulsion layer is a green-sensitive silver halide emulsion layer.

9. The color photographic light-sensitive material according to claim 1, wherein said at least one photographic layer is a light-insensitive photographic auxiliary layer.

10. The color photographic light-sensitive material according to claim 8, wherein said light-insensitive photographic auxiliary layer is an interlayer or a filter layer.

11. The color photographic light-sensitive material according to claim 1, wherein $R_1$ is said hydrogen atom.

12. The color photographic light-sensitive material according to claim 1, wherein $R_1$ is said —X—Y group.

13. The color photographic light-sensitive material according to claim 12, wherein X is said carbonyl group.

14. The color photographic light-sensitive material according to claim 12, wherein X is said sulfonyl group.

15. The color photographic light-sensitive material according to claim 1, wherein at least one of $R_2$, $R_3$ and $R_4$ is said alkylthio group.

16. The color photographic light-sensitive material according to claim 1, wherein said compound has the following formula:

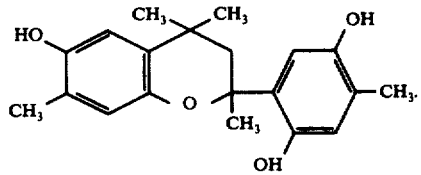

* * * * *